US012114695B2

United States Patent
Jacobs, Jr. et al.

(10) Patent No.: US 12,114,695 B2
(45) Date of Patent: Oct. 15, 2024

(54) ADDICTION CESSATION SYSTEMS, DEVICES, AND METHODS

(71) Applicant: Predictably Human, Inc., Westport, CT (US)

(72) Inventors: Robert Francis Jacobs, Jr., Norwalk, CT (US); J. Robert Geiman, Boston, MA (US); Douglas Philip Dean, Engelberg (CH); James Mcdowell Davis, Jr., Durham, NC (US); Carl David Marci, Boston, MA (US)

(73) Assignee: Predictably Human, Inc., Westport, CT (US)

( * ) Notice: Subject to any disclaimer, the term of this patent is extended or adjusted under 35 U.S.C. 154(b) by 275 days.

(21) Appl. No.: 17/650,783

(22) Filed: Feb. 11, 2022

(65) Prior Publication Data

US 2022/0256929 A1 Aug. 18, 2022

Related U.S. Application Data

(60) Provisional application No. 63/263,863, filed on Nov. 10, 2021, provisional application No. 63/261,638, (Continued)

(51) Int. Cl.
*A24F 40/30* (2020.01)
*A24F 40/42* (2020.01)
(Continued)

(52) U.S. Cl.
CPC .............. *A24F 40/30* (2020.01); *A24F 40/42* (2020.01); *A24F 40/51* (2020.01); *A24F 40/53* (2020.01);
(Continued)

(58) Field of Classification Search
CPC .......... A24F 40/10; A24F 40/30; A24F 40/42; A24F 40/51; A24F 40/53; A24F 40/57;
(Continued)

(56) References Cited

U.S. PATENT DOCUMENTS

| | | |
|---|---|---|
| 6,803,545 B2 | 10/2004 | Blake et al. |
| 8,256,433 B2 | 9/2012 | Gonda |

(Continued)

FOREIGN PATENT DOCUMENTS

| | | |
|---|---|---|
| CN | 105324045 | 2/2016 |
| CN | 110025049 | 7/2019 |

(Continued)

OTHER PUBLICATIONS

Machine translation of WO-2020078801-A1.*
International Search Report issued in application No. PCT/US2022/037213, dated Oct. 4, 2022.

*Primary Examiner* — Joseph D. Boecker
(74) *Attorney, Agent, or Firm* — KNOBBE, MARTENS, OLSON & BEAR LLP

(57) ABSTRACT

Systems and methods of an electronic cessation system. The system can include a mobile platform and a hand-held inhalation device including a flow sensor, aerosol sensing density and temperature sensors, a first, second, and third aerosolizer drivers, a rescue button, a power source, and a controller circuit comprising a hardware controller coupled to the power source, the sensors, the first, second, and third aerosolizer drivers, and the rescue button. The hardware controller is configured to perform a smoking cessation program that includes receiving input signals from the sensors, and the rescue button, and individually controlling the three aerosolizer drivers to provide aerosolizer generation signals to control a first, second and third aerosolizers of the aerosolizer pod to dynamically generate individually tailored aerosol mixtures from three substances in the aero- (Continued)

solizer pod based at least on the received input signals and the smoking cessation program information.

21 Claims, 29 Drawing Sheets

Related U.S. Application Data filed on Sep. 24, 2021, provisional application No. 63/203,324, filed on Jul. 16, 2021, provisional application No. 63/200,068, filed on Feb. 12, 2021.

(51) Int. Cl.
| | |
|---|---|
| *A24F 40/51* | (2020.01) |
| *A24F 40/53* | (2020.01) |
| *A24F 40/57* | (2020.01) |
| *A24F 40/60* | (2020.01) |
| *A24F 40/65* | (2020.01) |
| *A61M 11/04* | (2006.01) |
| *A61M 15/00* | (2006.01) |
| *A61M 15/06* | (2006.01) |
| *G06F 21/32* | (2013.01) |
| *A24F 47/00* | (2020.01) |
| *A61M 16/00* | (2006.01) |

(52) U.S. Cl.
CPC .............. *A24F 40/57* (2020.01); *A24F 40/60* (2020.01); *A24F 40/65* (2020.01); *A61M 11/042* (2014.02); *A61M 15/0065* (2013.01); *A61M 15/06* (2013.01); *G06F 21/32* (2013.01); *A24F 47/00* (2013.01); *A61M 2016/0033* (2013.01); *A61M 2205/121* (2013.01); *A61M 2205/3334* (2013.01); *A61M 2205/3368* (2013.01); *A61M 2205/3561* (2013.01); *A61M 2205/609* (2013.01)

(58) Field of Classification Search
CPC . A24F 47/00; A61M 11/042; A61M 15/0065; A61M 15/06; A61M 16/14; A61M 2016/0033; A61M 2205/121; A61M 2205/3334; A61M 2205/3368; A61M 2205/3561; A61M 2205/609; G06F 21/32
See application file for complete search history.

(56) References Cited

U.S. PATENT DOCUMENTS

| | | | |
|---|---|---|---|
| 8,689,803 | B2 | 4/2014 | Gonda |
| 8,899,230 | B2 | 12/2014 | Immel |
| 9,215,895 | B2 | 12/2015 | Bowen et al. |
| 9,901,123 | B2 | 2/2018 | Robinson et al. |
| 9,930,915 | B2 | 4/2018 | Worm et al. |
| 10,349,675 | B2 | 7/2019 | Choukroun et al. |
| D870,959 | S | 12/2019 | Leon Duque et al. |
| 10,737,041 | B1 | 8/2020 | Adelaar et al. |
| 10,772,353 | B2 | 9/2020 | Liu |
| 10,791,762 | B2 | 10/2020 | Liu |
| 10,849,364 | B2 | 12/2020 | Chen |
| 10,869,500 | B2 | 12/2020 | Chen |
| 10,893,703 | B2 | 1/2021 | Chen |
| 10,905,157 | B2 | 2/2021 | Lai |
| 10,905,167 | B2 | 2/2021 | Atkins et al. |
| D912,309 | S | 3/2021 | Bowen et al. |
| 10,952,468 | B2 | 3/2021 | Bowen et al. |
| 10,973,262 | B2 | 4/2021 | Li et al. |
| 10,986,868 | B2 | 4/2021 | Chen |
| 10,993,475 | B2 | 5/2021 | Chen |
| 11,006,672 | B2 | 5/2021 | Wei et al. |
| 11,013,271 | B2 | 5/2021 | Ding et al. |
| 11,033,694 | B2 | 6/2021 | Ballam et al. |
| 11,083,223 | B2 | 8/2021 | Chen |
| 2003/0098022 | A1 | 5/2003 | Nakao et al. |
| 2008/0138294 | A1 | 6/2008 | Gonda |
| 2014/0345631 | A1 | 11/2014 | Bowen et al. |
| 2015/0020824 | A1 | 1/2015 | Bowen et al. |
| 2016/0278435 | A1 | 9/2016 | Choukroun et al. |
| 2019/0364970 | A1 | 12/2019 | Choukroun et al. |
| 2020/0037669 | A1 | 2/2020 | Bowen et al. |
| 2020/0163382 | A1* | 5/2020 | Trzecieski ............. A24F 40/46 |
| 2020/0229512 | A1* | 7/2020 | Israel ...................... H05B 3/46 |
| 2020/0245687 | A1 | 8/2020 | Tsuji et al. |
| 2020/0305502 | A1 | 10/2020 | Ouyang |
| 2020/0315253 | A1 | 10/2020 | Legendy et al. |
| 2020/0367572 | A1 | 11/2020 | Hejazi et al. |
| 2020/0411839 | A1 | 12/2020 | Wang et al. |
| 2021/0000174 | A1 | 1/2021 | Huang |
| 2021/0000178 | A1 | 1/2021 | Chen |
| 2021/0186082 | A1 | 6/2021 | Bowen et al. |
| 2021/0268215 | A1* | 9/2021 | Israel .................. A61M 11/042 |
| 2022/0160031 | A1* | 5/2022 | Griffin .................. A24F 40/42 |
| 2022/0256929 | A1 | 8/2022 | Jabobs et al. |
| 2023/0023805 | A1* | 1/2023 | Jacobs, Jr. .......... A61M 15/009 |
| 2023/0037987 | A1* | 2/2023 | Benning ................ A24F 40/57 |

FOREIGN PATENT DOCUMENTS

| | | | |
|---|---|---|---|
| CN | 111264908 | | 6/2020 |
| WO | WO 2016/000136 | | 1/2016 |
| WO | WO-2020078801 A1 * | 4/2020 | ............. A24F 40/10 |
| WO | WO 2020/252810 | | 12/2020 |
| WO | WO 2020/254313 | | 12/2020 |
| WO | WO 2021/003438 | | 1/2021 |
| WO | WO 2021/013208 | | 1/2021 |

* cited by examiner

```
                          600
                         /
    ┌─────────────────────────┐
    │   OPERATE A CESSATION   │── 605
    │ PROGRAM ON A HANDHELD   │
    │    CESSATION SYSTEM     │
    └────────────┬────────────┘
                 │
    ┌────────────┴─────────────┐
    │ CONTROL AEROSOL GENERATED BY │
    │   EACH OF THE THREE OR MORE  │
    │  AEROSOLIZERS IN THE CESSATION│── 610
    │ SYSTEM, BASED ON THE CESSATION│
    │  PROGRAM, TO FORM AN AEROSOL │
    │           MIXTURE            │
    └──────────────────────────────┘
```

┌─────────────────────────────┐
        │   PROVIDE A HAND-HELD       │ ─── 705
        │ CESSATION SYSTEM HAVING     │
        │   AN AEROSOLIZER SYSTEM     │
        │   WITH THREE AEROSOLIZERS   │
        │  EACH INCLUDING A DIFFERENT │
        │          SUBSTANCE          │
        └──────────────┬──────────────┘
                       │
        ┌──────────────┴──────────────┐
        │ CONTROL THE AEROSOL PRODUCED BY │ ─── 710
        │ EACH OF THE THREE AEROSOLIZERS TO │
        │ FORM AN AEROSOL MIXTURE IN AN │
        │ AEROSOL MIXING CHAMBER, BASED ON A │
        │ CESSATION PROGRAM AND USING │
        │ INFORMATION FROM PLURALITY OF │
        │ SENSORS ON THE HAND-HELD │
        │ CESSATION SYSTEM │
        └─────────────────────────────┘
```

FIG. 6C

B: PERSONALIZATION PARAMETERS THAT INFLUENCE HOW THE BODY PROCESSES NICOTINE

| | FACTORS INFLUENCING NICOTINE METABOLISM | | | | PRIORITIZATION |
|---|---|---|---|---|---|
| | DESCRIPTION | CATEGORY | QUANTIFICATION METHOD | REMARKS | |
| 4.0 | DOSE<br>4.0.1 EXPERIENCE FREQUENCY<br>4.0.2 PUFF TOPOLOGY<br>4.0.3 SITE OF DEPOSITION | INPUT | MEASURE - DEVICE DATA<br>MEASURE - DEVICE DATA | DOSE = F(PERSONA)<br>DEVICE DATA LOGGING AND UPLOAD TO ANALYSIS & REPORTING APPLICATIONS. | PRIMARY PARAMETER: PERSONA CLASSIFICATION AT ONBOARDING, INCLUDING DEVICE DATA LOGGING FOR ROLLING DOSAGE CALCULATION. |
| 4.1 | ADME RESPONSE<br>4.1.1 DISTRIBUTION<br>4.1.2 CENTRAL ABSORPTION<br>4.1.3 CENTRAL TISSUE RESERVOIRS (BOUND↔FREE)<br>4.1.4 SITE OF ACTION (BOUND↔FREE)<br>4.1.5 UNWANTED SITE OF ACTION (BOUND↔FREE)<br>4.1.6 BIOTRANSFORMATION<br>4.1.7 CENTRAL ELIMINATION RATE CONSTANT (ERC)<br>4.1.8 CENTRAL-PERIPHERAL ERC<br>4.1.9 PERIPHERAL ABSORPTION<br>4.1.10 PERIPHERAL TISSUE RESERVOIRS (B↔F)<br>4.1.11 PERIPHERAL-CENTRAL ERC | PRIMARY | NMR<br>NMR<br>NMR<br>NMR<br>NMR<br>NMR<br>NMR<br>NMR<br>NMR<br>NMR<br>NMR | PERSONA = F(ADME)<br>GENOMIC INDICATOR: SALIVARY SAMPLE AND LABORATORY ANALYSIS.<br><br>SLOWEST - AVERAGE - FASTEST<br>NMR < 0.26   0.31   NMR > 0.54 | PRIMARY PARAMETER: NMR ANALYTICAL RESULT FOR GENOMIC INDICATORS. |
| 4.2 | SEX | PRIMARY | NMR | GENOMIC INDICATOR: SAMPLE AND ANALYSIS. | |
| 4.3 | RACIAL/ETHNIC PROFILE | PRIMARY | NMR | GENOMIC INDICATOR: SAMPLE AND ANALYSIS. | |
| 4.4 | AGE | PRIMARY | NMR | NMR VARIABLE: ALSO A PRIMARY INPUT TO TAPER RATE. | PRIMARY PARAMETER: PRIMARY DETERMINANT OF TAPER RATE. |

FIG. 7B-1

| | | | | SECONDARY PARAMETERS & MODIFYING FACTORS: • NOTE AT ONBOARDING WITH CLINICIAN INTERVIEW. OR NOTE AT ONBOARDING WITH PERSONAL INPUT. |
|---|---|---|---|---|
| 4.5 | MENOPAUSAL STATUS<br>4.5.1 PRE<br>4.5.2 PERI<br>4.5.3 POST | SECONDARY | ONBOARDING/INTERVIEW | NMR VARIABLE. STATUS MAY BE TRANSIENT OR VARIABLE OVER THE DURATION OF THE CESSATION PROGRAM. THEREFORE DYNAMICS ASSOCIATED WITH SMOKING CESSATION NEED TO BE FACTORED. |
| 4.6 | CO-MORBIDITIES | SECONDARY | ONBOARDING/INTERVIEW | NMR VARIABLE. ACCOUNTED IN NMR RESULT |
| 4.7 | MEDICATIONS<br>4.6.1 INDUCERS<br>4.6.2 INHIBITORS | SECONDARY | ONBOARDING/INTERVIEW | POTENTIAL IMPACT NEEDS EXPERT ASSESSMENT AT ONBOARDING TIME. QUICKLY CLEARED MEDS MAY NOT IMPACT NMR, BUT WILL INFLUENCE BIOTRANSFORMATION. IN ALL BUT EXCEPTIONAL CIRCUMSTANCES SHOULD BE ACCOUNTED IN NMR RESULT. |
| 4.8 | LIFESTYLE FACTORS<br>4.10.1 SMOKER<br>4.10.2 MENTHOL SMOKER<br>4.10.3 DIET<br>4.10.4 EXERCISE<br>4.10.5 CHRONOPHARMACOKINETICS | SECONDARY | ONBOARDING/INTERVIEW | NMR VARIABLES. CHANGES IN THESE FACTORS WILL ALTER NICOTINE METABOLISM. THEREFORE DYNAMICS ASSOCIATED WITH SMOKING CESSATION MAY NEED TO BE FACTORED. SHOULD BE ACCOUNTED IN NMR RESULT. |
| 4.9 | BODY MASS INDEX | TERTIARY | ONBOARDING/NMR MEASURE | NMR VARIABLE. NON-GENOMIC PERSONAL INDICATOR – ACCOUNTED IN NMR RESULT. |
| 4.10 | ADIPOSE TISSUE PROPORTION | TERTIARY | ONBOARDING/NMR MEASURE | NMR VARIABLE. NON-GENOMIC PERSONAL INDICATOR – ACCOUNTED IN NMR RESULT. |
| 4.11 | ENVIRONMENTAL FACTORS | QUATERNARY | ONBOARDING/INTERVIEW/NMR MEASURE | NMR VARIABLE. NON-GENOMIC ENVIRONMENTAL INDICATOR – SHOULD BE ACCOUNTED IN NMR RESULT. |

TERTIARY & QUATERNARY PARAMETERS:
• NOTED AT ONBOARDING ONLY IF EXCEPTIONAL.

FIG. 7B-2

C: Biological Co-Factors: The Four Key Personalization Parameters Determine Three Critical Variables of the Cessation Liquid And Aerosol (P1)
- The dose of nicotine per experience is determined by:
(V1) Nicotine concentration
- How the user puffs dose Nicotine deposited in the body is:
- Absorbed
- Distributed
- Metabolized
- Eliminated in an individual manner that is determined by genomics, personal and environmental parameters, then the metabolic by-products are:

(V2) Aerosol droplet size (Deposition)
(P2) Site of nicotine deposition
(P3) How quickly the nicotine is absorbed
(P4) How rapidly the nicotine is metabolized
(V3) Free nicotine ratio (Bioavailability)

Excretion from body (NMR)

FIG. 7G

F: ρ - Concentration levels of nicotine mapped to persona profile and metabolism rate

|  | Reduced | Typical | Enhanced |
|---|---|---|---|
| Intense | Moderate Concentration | High Concentration | High Concentration |
| Typical | Low Concentration | Moderate Concentration | High Concentration |
| Mid | Low Concentration | Low Concentration | Moderate Concentration |

Psychosocial Persona Parameters (vertical axis) · Biological Persona Parameters (horizontal axis)

FIG. 7L

F: δ - Aerosol droplet size mapped to persona profile and metabolism rate

▽ = Aerosol droplet dia. ≤ 1μ (pulmonary deposition)

| | Reduced | Typical | Enhanced |
|---|---|---|---|
| Intense | Moderate Concentration | High Concentration | High Concentration |
| Typical | Low Concentration | Moderate Concentration | High Concentration |
| Mild | Low Concentration | Low Concentration | Moderate Concentration |

High Bioavailability Nicotine Mix
Reduced Bioavailability Nicotine Mix
Low Bioavailability Nicotine Mix Psychosocial Persona Parameters
Biological Persona Parameters Aerosol droplet dia. ≥ 2μ (buccal deposition) = △

FIG. 7N

G: Based on the cessation start point, age, and behavioral information related to triggers, stresses, anxiety, depression, alcohol consumption and social cue responses, a taper path, taper rate, and program duration is uniquely determined

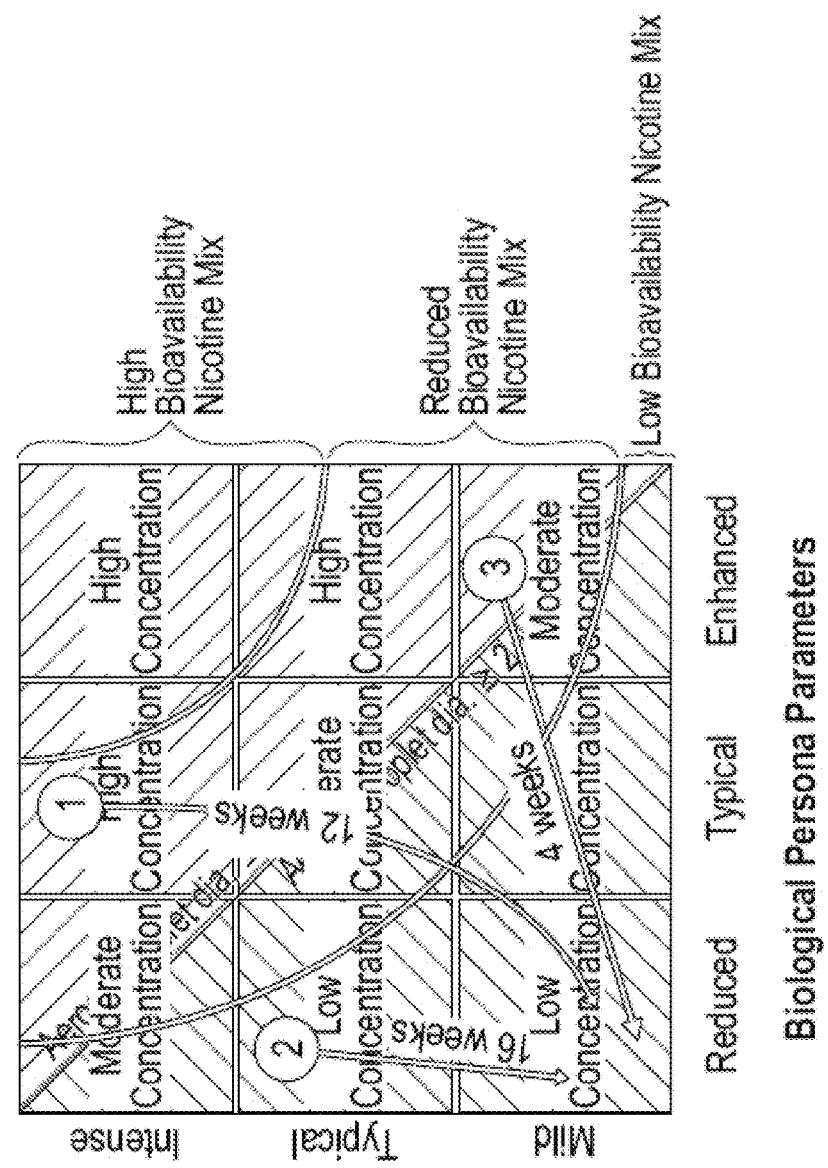

User 1: Taper from high dose, high bioavailability, pulmonary deposition, to very low dose, low bioavailability, buccal deposition over 12 weeks. User changes consumable category three times.

User 2: Taper from low dose, low bioavailability, buccal deposition, to very low dose over 16 weeks. Consumable category remains the same over the 16 week quit period.

User 3: Taper from moderate dose, reduced bioavailability, pulmonary deposition to very low dose, low bioavailability, buccal deposition over 4 weeks. User has two consumable category changes over four weeks.

FIG. 7P

ADDICTION CESSATION SYSTEMS, DEVICES, AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

This disclosure relates to systems, devices, and methods for assisting a user for treating an addiction. More particularly, this invention relates to systems, devices, and methods for implementing an addiction cessation program that is individually tailored for a user and can be dynamically changed based on day-to-day sensed characteristics of the user's actions and progress in the cessation program.

Description of the Related Art

Addictions can result in physical and mental harm. For example, smoking causes many diseases including cancer, heart disease, stroke, lung diseases, diabetes, emphysema and chronic bronchitis. Smoking is also known to increase a person's risk for tuberculosis, certain eye diseases, and problems of the immune system, including rheumatoid arthritis. smoking is one of the most prevalent sources of preventable death worldwide. People who don't smoke but are near a person who is smoking may also be afflicted with one of these diseases through secondary smoke.

Smoking and vaping (which is, for ease of reference, are both generally referred to herein as "smoking" unless context or specific language indicates otherwise) are highly addictive, and quitting smoking is difficult. Many aids have been developed to quit smoking. For example, nicotine patches and nicotine gum may help a person to quit smoking. Certain devices (e.g., electronic cigarettes) have been developed as an aid to quit smoking, or at least somewhat lower health risks, by providing a less harmful source of inhaled nicotine. Such devices are generally used in a similar manner for everyone, even though different people have different biological factors and psychological factors related to smoking. Also, such devices cannot dynamically provide tailored aerosol mixtures based as required by a sophisticated individual cessation program. In addition, such devices cannot adequately monitor the use of the device and provide feedback to the cessation system to increase accuracy and efficiency. Furthermore, such devices do not allow a user to, when needed, address an overwhelming addiction urge, where it is monitored and subsequently dynamically affects the cessation program. Accordingly, there is a need for an improved process to treat addictions, for example, help smokers quit smoking, which addresses an individual's biological and psychological factors in a tailored smoking cessation process.

SUMMARY

The systems, methods, and devices described herein each have several aspects, no single one of which is solely responsible for its desirable attributes. Without limiting the scope of this disclosure, several non-limiting features will now be discussed briefly. The methods and techniques described herein relate to systems, devices, and methods for treating addiction, for example, for helping a person to stop smoking.

One innovation includes a smoking cessation system that includes a cessation device having a housing which has a distal end, which is positioned away from the user when in-use, and a proximal end which is positioned towards the user. A channel in the housing has an opening on a distal end for receiving air and an opening positioned on a proximal end of the channel to communicate air to an aerosolizer pod coupled to the housing, for example, that has been inserted into the proximal end of the housing. An aperture on the housing proximal end is configured to receive the aerosolizer pod therein, the housing configured to at least partially surround the aerosolizer pod when the aerosolizer pod is positioned in the housing. The cessation device includes sensors that monitor the use of the device. Data collected from the sensors provides feedback to a hardware processor on the cessation device. Sensor information can be communicated from the hardware processor to a mobile platform and/or a server in the cessation system to monitor a user's progress in their cessation program, and can be used to dynamically change the cessation program. In an example, sensor data is used to modify the cessation program to change an aerosol mixture provided to a user by changing the percentage of three substances in the aerosol mixture. In another example, the cessation program is modified to change the droplet size of one or more of the substances in an aerosol mixture. The sensors can include a flow sensor positioned to sense air flowing through the channel, a first, second, and third density sensor configured to sense a density of aerosol generated by a first, second, and third aerosolizer, respectively, in an aerosolizer system of the aerosolizer pod, and communicate a corresponding signal. The sensors further include a first, second, and third temperature sensor configured to sense a temperature of aerosol generated by the first, second, and third aerosolizer, respectively, and communicate a corresponding signal. The cessation device also includes a first, second, and third aerosolizer driver configured to electrically couple to the first, second, and third aerosolizer, respectively in an aerosolizer pod coupled to the cessation device. The cessation device further includes a "rescue button" which a user can activate when additional use of the cessation device is needed (above the planned cessation program scheduled use). The cessation device can also include a power source and a controller circuit coupled to the power source. The controller circuit can include a hardware controller coupled to the flow sensor, the first, second and third density sensors, the first, second and third temperature sensors, the first, second, and third aerosolizer drivers, and the rescue button. The hardware controller can include a hardware processor (e.g., a microprocessor) and a non-transitory computer readable medium in communication with the hardware controller. The computer readable medium is configured to store smoking cessation program information, and to store executable instructions that, when executed, configure the hardware controller to perform a smoking cessation program that includes receiving input signals from the flow sensor, the first, second, and third density sensors, the first, second, and third temperature sensors, and the rescue button, and individually controlling the three aerosolizer drivers to provide aerosolizer generation signals to control the first, second and third aerosolizers of the aerosolizer pod to generate an aerosol mixture based at least on the smoking cessation program information.

Various embodiments can include one or more other features. For example, in some embodiments the cessation system further includes the aerosolizer pod, which has a distal end and a proximal end, and includes an intake port on the distal end for receiving air flowing through the channel, an exhaust port on the proximal end for communicating the aerosol mixture out of the aerosolizer pod, an aerosolizer system comprising the first, second, and third aerosolizer, the first, second, and third aerosolizers including an electrical connection that electrically couples to the first, second, and third aerosolizer drivers, respectively, when the aerosolizer pod is received into the housing. In some embodiments, the aerosolizer pod further comprises an aerosol mixing chamber having walls that define a mixing space, the mixing chamber having intake openings in fluid communication with the first, second and third aerosolizer and an exhaust opening in fluid communication with the pod exhaust port such that aerosol generated by the first, second and third aerosolizer can enter the mixing chamber via the intake openings, mix together, and be communicated to the user via the pod exhaust port. In some embodiments, the first aerosolizer includes a first container for holding a first substance, a first heater configured to generate aerosol from the first substance based on signals received from the first aerosolizer driver, and a first passage in fluid communication with the heater and the mixing chamber for communicating aerosol generated by the first heater to the mixing chamber, the second aerosolizer includes a second container for holding a second substance, a second heater configured to generate aerosol from the second substance based on signals received from the second aerosolizer driver, and a second passage in fluid communication with second heater and the mixing chamber for communicating aerosol generated by the second heater to the mixing chamber, and the third aerosolizer includes a third container for holding a third substance, a third heater configured to generate aerosol from the third substance based on signals received from the third aerosolizer driver, and a third passage in fluid communication with the third heater and the mixing chamber for communicating aerosol generated by the third heater to the mixing chamber. In some embodiments of a cessation system, the first, second and third density sensors are optical sensors, wherein the first, second and third passages include a sensing port, wherein the first, second and third density sensors are positioned adjacent to the sensing ports of the first passage, the second passage, and the third passage when the aerosolizer pod is received into the housing.

In some embodiments of a cessation system, the controller circuit further comprises a transceiver, and an antenna coupled to the transceiver, the transceiver configured to receive smoking cessation program information from a mobile platform via the antenna. In some embodiments, the cessation system further comprises the mobile platform, the mobile platform being configured to communicate with the cessation device to receive operational use information from the cessation device and provide updated smoking cessation program information to the cessation device. In some embodiments, the operational use information is based at least in part on one or more of signals received by the hardware controller from the flow sensor. In some embodiments, the operational use information is additionally based at least in part on one or more of signals received by the hardware controller from the rescue button. In some embodiments, the operational use information is additionally based at least in part on one or more of signals received by the hardware controller from the density sensors and the temperature sensors. In some embodiments, the cessation system further includes a cloud-based back-end computing system configured to receive operational use information from the mobile platform and provide the updated smoking cessation program information to the mobile platform. In some embodiments, aerosolizer pod further comprises an ID chip, and wherein the cessation device further comprises an aerosolizer pod interface configured to sense the ID chip and communicate the ID chip to the hardware controller. In some embodiments, a cessation system can further comprise a fingerprint sensor coupled to the hardware controller, wherein the executable instructions further configure the hardware controller receive an input from the fingerprint sensor and activate the cessation device for use only when the fingerprint matches an authorized previously provided fingerprint. In some embodiments, a cessation system can further comprise an ambient temperature sensor coupled to the hardware controller and an ambient pressure sensor coupled to the hardware controller, wherein the hardware controller is further configured to provide aerosolizer generation signals based at least in part on the signal from the ambient temperature sensor and the ambient pressure sensor.

In some embodiments of a cessation system, the hardware controller provides aerosolizer control signals to control at least one of the first, second, and third aerosolizers to generate aerosol having a desired drop size based on the smoking cessation program information. In some embodiments, the hardware controller provides aerosolizer control signals to the first, second, and third aerosolizer drivers to control each of the first, second, and third aerosolizers to generate aerosol having a desired drop size based on the smoking cessation program information. In some embodiments, the hardware controller provides aerosolizer control signals to control the first, second, and third aerosolizers to generate desired aerosol mixture having a desired amount of a first substance, a second substance, and a third substance based on the smoking cessation program information. In some embodiments, the hardware controller is further configured to provide signals to the first, second, and third aerosolizer drivers to individually and dynamically control the first aerosolizer, the second aerosolizer, and the third aerosolizer, respectively, to produce the aerosol mixture having a concentration of a first substance, a concentration of a second substance, and a concentration of a third substance based on the smoking cessation program information. In some embodiments, the hardware controller is further configured to provide signals to the first, second, and third aerosolizer drivers to individually and dynamically control the first aerosolizer to produce a first aerosol having droplets of a first size, the second aerosolizer to produce a second aerosol having droplets of a second size, and the third aerosolizer to produce a third aerosol having droplets of a third size. In some embodiments, hardware controller is further configured to execute instructions to perform the smoking cessation program based on information determined from the flow sensor including puff duration, puff interval, puff volume, and/or puff profile.

Another innovation includes a method for smoking cessation, the method comprising providing a smoking cessation device including a housing having a distal end and a proximal end, a channel in the housing, the channel having an opening on a distal end of the channel for receiving air and an opening positioned on a proximal end of the channel to communicate air to an aerosolizer pod coupled to the housing, the aerosolizer pod including a first aerosolizer having a first container holding a first substance, a second aerosolizer having a second container holding a second substance that is different from the first substance, and a third aerosolizer having a third container holding a third substance different from the first and second substances, an aperture on the proximal end of the housing configured to receive the aerosolizer pod therein, the housing configured to at least partially surround the aerosolizer pod when the aerosolizer pod in positioned in the housing, a flow sensor positioned to sense air flowing through the channel, a first, second, and third density sensor configured to sense a density of aerosol generated by a first, second, and third aerosolizer, respectively, and communicate a corresponding signal, a first, second, and third temperature sensor configured to sense a temperature of aerosol generated by the first, second, and third aerosolizer, respectively, and communicate a corresponding signal, a first, second, and third aerosolizer driver configured to electrically couple to the first, second, and third aerosolizer, respectively, a rescue button, a power source, and a controller circuit coupled to the power source, the controller circuit comprising a computer hardware controller coupled to the flow sensor, the first, second and third density sensors, the first, second and third temperature sensors, the first, second, and third aerosolizer drivers, and the rescue button, the controller including a hardware processor and a non-transitory computer readable medium in communication with the hardware controller, the computer readable medium having smoking cessation program information stored therein. The method further includes providing signals, from the controller, to the first, second and third aerosolizer drivers to dynamically and individually control the first, second and third aerosolizers to generate aerosol mixtures that are dynamically changed over a period of time to have different drop sizes and different concentration of the first, second and third substance, based on received input signals from one or more of the flow sensor, the first, second, and third density sensors, the first, second, and third temperature sensors, the rescue button, and the smoking cessation program information.

Another innovation includes method for smoking cessation, the method comprising providing signals, from a hardware controller in a hand-held cessation device, to a first, second and third aerosolizer driver in the hand-held cessation device to dynamically and individually control a first, second and third aerosolizer, in an aerosolizer pod coupled to the hand-held cessation device, to generate aerosol mixtures that are dynamically changed over a period of time to have different drop sizes and different concentration of a first, second and third substance contained in the first, second, and third aerosolizer, respectively, based at least in part on received input signals from one or more of a flow sensor, a density sensor, a temperature sensor, a rescue button, and on a smoking cessation program information stored in a non-transitory computer readable medium coupled to the hardware controller, wherein the method is executed by the controller executing computer executable instructions stored on the non-transitory computer readable medium, wherein the executable instructions when executed cause the hardware controller to perform a smoking cessation program that includes providing the signals to the first, second, and third aerosolizer drivers.

Another innovation includes an electronic cessation system for assisting in a smoking or vaping cessation program. In some embodiments the cessation system can include a housing having a distal end and a proximal end, the housing including a conduit having an opening on the distal end of the housing for receiving air and an opening for communicating air to an aerosolizer system; an opening on the proximal end of the housing configured to receive the aerosolizer system; a controller including a hardware processor and a non-transitory memory in electrical communication with the controller, the memory having executable instructions that configure the hardware processor to perform a cessation program; an aerosolizer system removably coupleable to the housing, the aerosolizer system having an intake on a distal end for receiving air flowing through the conduit and having an exhaust on a proximal end for providing an aerosol from the aerosolizer system, and an aerosol mixing chamber. The aerosolizer system includes two or more aerosolizers, each aerosolizer including a heating element, a container in fluid communication with the heating element, a passage configured to communicate aerosol generated by the heating element to the aerosol mixing chamber, the passage having a distal end and a proximal end, the aerosol mixing chamber being coupled to the proximal end of each passage such that the aerosol mixing chamber is in fluid communication with aerosol in each passage. The cessation system further can include a flow meter in electrical communication with the controller, the flow meter positioned to sense air flowing through the conduit, a density sensor associated with each of the two or more aerosolizers, each aerosol density sensor positioned to measure aerosol density in the passage of its associated aerosolizer between the heater and the aerosol mixing chamber, each density sensor being in electrical communication with the controller, and an ambient temperature sensor in electrical communication with the controller. where the controller is configured to control the aerosol produced by each of the two or more aerosolizers to form an aerosol mixture in the aerosol mixing chamber, based on the cessation program, and using information from the flow meter, the temperature sensor, and the density sensors.

Such systems are further characterized by, or such system can further include a number of aspects (features or limitations) which are disclosed in summary below and/or discussed herein. The cessation system can further include two or more aerosolizer driver, each aerosolizer driver associated with an aerosolizer in the aerosolizer system, each aerosolizer driver connected to the controller and configured to couple to the aerosolizer system when the aerosolizer system is coupled to the housing and provide signals to control aerosol generation from its associated aerosolizer. The cessation system can further include electrical connections configured couple each heating element to an associated aerosolizer driver, the electrical connections providing power to operate the heating elements and/or control signals for controlling the heating elements. The cessation system can further include a power source coupled to the controller. In some embodiments, the battery provides power to the controller and/or the aerosolizer system. The aerosolizer system can be removably coupled to the housing such that a first aerosolizer system can be coupled to the housing, the first aerosolizer system can be de-coupled from the housing, and a second aerosolizer system can be coupled to the housing. In some embodiments, at least a portion of the aerosolizer system resides inside the housing when the aerosolizer system is coupled to the housing. In some embodiments, at least a portion of aerosolizer system resides outside the housing when the aerosolizer system is coupled to the housing. In some embodiments, the controller is configured to determine a temperature value of the heating element, wherein the controller is configured to control the aerosol produced by each of the aerosolizers based in part on information from the temperature value of the heating element. In some embodiments, the system further includes an ambient pressure sensor in electrical communication with the controller, wherein the controller is configured to control the aerosol produced by each of the aerosolizers based in part on information from the ambient pressure sensor. In some embodiments, the controller further includes a transceiver coupled to the controller. In some embodiments, the cessation system further includes an antenna coupled to the transceiver. The controller includes one or more hardware processors configured to execute instructions to perform a cessation program based on information determined from the flow sensor including puff duration, puff interval, puff volume, and/or puff profile. In some embodiments, the hardware processor is configured to execute instructions to perform a cessation program based on information determined from the flow sensor including puff duration, puff interval, and puff volume. In some embodiments, the controller determines a puff volume, based on information the controller receives from the flow sensor. In some embodiments, controller determines a puff duration based on information the controller receives from the flow sensor. In some embodiments, the controller determines a puff frequency based on information the controller receives from the flow sensor. In some embodiments, the controller determines one or more of a puff volume, a puff duration, and a puff frequency based on information the controller receives from the flow sensor. In some embodiments, the two or more aerosolizers of the aerosolizer system comprises a first aerosolizer, second aerosolizer, and a third aerosolizer, and wherein the controller is configured to control the first aerosolizer, second aerosolizer, and a third aerosolizer to produce the aerosol mixture based on the cessation program.

In some embodiments, the two or more aerosolizers of the aerosolizer system include a first aerosolizer having a first substance in a first container, second aerosolizer having a second substance in a second container, and a third aerosolizer having a third substance in a third container, wherein the controller is configured to individually and dynamically control the first aerosolizer to produce a first aerosol, the second aerosolizer to produce a second aerosol, and a third aerosolizer to produce third aerosol based on the cessation program. In some embodiments, the first substance has a first nicotine freebase ratio and the second substance has a second nicotine freebase ratio. In some embodiments, the controller is configured to, based on the cessation program, individually and dynamically control the first aerosolizer, the second aerosolizer, and the third aerosolizer to produce the aerosol mixture having a concentration of the first substance, a concentration of the second substance, and a concentration of the third substance based on the cessation program. In some embodiments, the controller is configured to, based on the cessation program, individually and dynamically control the first aerosolizer to produce the first aerosol to have droplets of a first size, the second aerosolizer to produce the second aerosol having droplets of a second size, and the third aerosolizer to produce the third aerosol having droplets of a third size. In some embodiments, at least one of the first size, second size, and third size are different sizes from the other two. In some embodiments, the first size, second size, and third size are substantially the same size. In some embodiments, the first size, the second size, and the third size are less than or equal to 1 µm for a first portion of the cessation program and the first size, the second size, and the third size are greater than or equal to 5 µm and less than or equal to 10 µm for a second portion of the cessation program. In some embodiments, the controller is configured to, based on the cessation program, individually and dynamically control the first aerosolizer, the second aerosolizer, and the third aerosolizer to produce the aerosol mixture having a certain monoprotonated nicotine concentration based on the cessation program. In some embodiments, the controller is configured to, based on the cessation program, individually and dynamically control the first aerosolizer, the second aerosolizer, and the third aerosolizer to produce the aerosol mixture having a certain total nicotine concentration based on the cessation program.

In some embodiments, the controller is configured to receive cessation program information from another computing device via the transceiver. In some embodiments, the cessation program includes parameters that are used to control the aerosolizer system to generate the aerosol mixture to have varying concentrations of the substances contained in the aerosolizer system at different points in a period of time during a cessation schedule for a certain person, and wherein the parameters are changed during the cessation schedule based on sensed information during the cessation program. In some embodiments, the parameters are associated with droplet size for aerosol generated by the first, second, and third aerosolizer. In some embodiments, the parameters are associated with a nicotine concentration of the aerosol mixture. In some embodiments, the cessation system can further include an aerosolizer system interface configured to communicate signals from the controller to the aerosolizer system to operate each of the heating elements to generate the aerosol mixture having a desired amount of aerosol from each of the two or more aerosolizers in the aerosolizer system.

Another innovation includes an aerosolizer system for use in an electronic cessation system for assisting in a smoking or vaping cessation program, the aerosolizer system including a distal end and an intake for receiving air, a proximal end having an exhaust for providing an aerosol to a user, an aerosol mixing chamber. The aerosolizer system can further include two or more aerosolizers, each aerosolizer including a heating element, a container in fluid communication with the heating element, a passage configured to communicate aerosol generated by the heating element to the aerosol mixing chamber, the passage having a distal end and a proximal end, the aerosol mixing chamber being coupled to the proximal end of the passage such that the aerosol mixing chamber is in fluid communication with aerosol in the passage of each of the aerosolizers in the aerosolizer system. In some embodiments, the aerosolizer system is configured to be removably coupleable to a housing of a cessation system. In some embodiments, the distal end of the aerosolizer system is configured to be removably coupleable to a housing of a cessation system. In some embodiments, the aerosolizer system further includes an aerosolizer system chip controller configured to receive signals from a controller in the housing and to drive heating elements to generate aerosol. In some embodiments, the aerosolizer system further includes three aerosolizers, each aerosolizer having a heating element and a container containing a substance. In some embodiments, each aerosolizer further includes a passage configured to communicate aerosol generated by the heating element to the aerosol mixing chamber. In some embodiments, the aerosolizer system further includes electrical connections configured couple each heating element to an associated aerosolizer driver, the electrical connections configured to communicate power to operate the heating elements and control signals for controlling the heating elements.

Another innovation includes an electronic cessation system for assisting in a smoking or vaping cessation program. The system can include a housing having a distal end and a proximal end, the housing including a conduit having an opening on the housing for receiving air and an opening for communicating air to an aerosolizer system, an opening on the housing configured to receive the aerosolizer system, a controller including a hardware processor and a non-transitory memory in electrical communication with the controller, the memory having executable instructions that configure the hardware processor to perform a cessation program, an interface to couple to an aerosolizer system having two or more aerosolizers, a flow meter in electrical communication with the controller, the flow meter positioned to sense air flowing through the conduit, a density sensor associated with each of the two or more aerosolizers of the aerosolizer system, each density sensor being in electrical communication with the controller, and an ambient temperature sensor being in electrical communication with the controller, where the controller is configured to control the aerosol produced by each of the two or more aerosolizers to form an aerosol mixture in an aerosol mixing chamber of the aerosolizer system, based on the cessation program, and using information from the flow meter, the temperature sensor, and the density sensors.

Another innovation is a method of operating a smoking or vaping cessation system, the method comprising providing a smoking cessation system (for example, in any of the embodiments and having features described herein) and controlling aerosol produced by each of the three or more aerosolizers to form an aerosol mixture in an aerosol mixing chamber, based on a cessation program, and based on information received from a flow meter, an ambient temperature sensor, and density sensors.

Another innovation includes a method of operating a handheld smoking or vaping cessation system, the method comprising controlling aerosol generated by each of the three or more aerosolizers of an aerosolizer system to form an aerosol mixture in an aerosol mixing chamber, the aerosol mixing chamber being in fluid communication with an exhaust opening for providing the aerosol mixture to a user.

Another innovation is a non-transitory computer readable medium having instructions stored thereon, that when executed by a computer hardware processor cause the computer hardware processor to perform a portion of, or all of, any of the methods described herein.

In an example, an innovation includes a non-transitory computer readable medium for operating a smoking cessation system, the computer readable medium having program instructions for causing a hardware processor to perform a method of providing signals, from a hardware controller in a hand-held cessation device, to a first, second and third aerosolizer driver in the hand-held cessation device to dynamically and individually control a first, second and third aerosolizer, in an aerosolizer pod coupled to the hand-held cessation device, to generate aerosol mixtures that are dynamically changed over a period of time. In another example, an innovation includes a non-transitory computer readable medium for operating a smoking cessation system, the computer readable medium having program instructions for causing a hardware processor to perform a method of providing signals, from a hardware controller in a hand-held cessation device, to a first, second and third aerosolizer driver in the hand-held cessation device to dynamically and individually control a first, second and third aerosolizer, in an aerosolizer pod coupled to the hand-held cessation device, to generate aerosol mixtures that are dynamically changed over a period of time, including controlling the aerosol mixture having to have one or more of different drop sizes and different concentration of a first, second and third substance contained in the first, second, and third aerosolizer, respectively, based at least in part the cessation program, and which can also be based on received input signals from one or more of a flow sensor, a density sensor, a temperature sensor, a rescue button, and on a smoking cessation program information stored in the non-transitory computer readable medium coupled to the hardware controller.

Additional embodiments of the disclosure are described below in reference to the appended claims, which may serve as an additional summary of the disclosure.

In various embodiments, systems disclosed that a computer readable storage medium having program instructions embodied therewith, and one or more processors configured to execute the program instructions to cause the one or more processors to perform operations comprising one or more aspects of the above- and/or below-described embodiments (including one or more aspects of the appended claims). The cessation program can be included on server system, or can be included on an application-specific integrated circuit (ASIC) or other integrated circuit chips that are customized to include data flow processing and classifying, and such ASIC's or other integrated circuit chips can be included in a network or network element.

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a non-transitory computer readable storage medium are disclosed, wherein the computer readable storage medium has program instructions embodied therewith, the program instructions executable by one or more processors to cause the one or more processors to perform operations comprising one or more aspects of the above-described and/or below-described embodiments (including one or more aspects of the appended claims).

BRIEF DESCRIPTION OF THE DRAWINGS

The features and advantages of the systems and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings are not intended to depict every feature, structure, and/or component of actual embodiments of the systems and components illustrated, are they intended to depict relative dimensions of the illustrated elements, and the drawings may not be drawn to scale.

FIG. 6B is a flowchart illustrating an example of a smoking cessation process, according to one embodiment.

FIG. 6C is a flowchart illustrating another example of a smoking cessation process, according to one embodiment.

FIGS. 7B-1 and 7B-2 is a table illustrating personalization parameters that influence how the body processes nicotine.

FIG. 7G is a diagram illustrating an example of how the four key personalization parameters determine three critical variables.

FIG. 7L is a diagram illustrating concentration levels of nicotine mapped to persona profile and metabolism rate.

FIG. 7N is a diagram illustrating aerosol droplet size mapped to persona profile and metabolism rate.

FIG. 7O is a diagram illustrating a starting combination of cessation liquid variables defined for a unique user.

FIG. 7P is a diagram illustrating variables that can be applied to uniquely tailor a cessation program.

DETAILED DESCRIPTION OF CERTAIN INVENTIVE ASPECTS

The detailed description of various exemplary embodiments below, in relation to the drawings, is intended as a description of various aspects of the various exemplary embodiments, components, and methods implemented with a smoking cessation system, and is not intended to represent the only aspects in which the various exemplary embodiments described herein may be practiced. The detailed description includes specific details for the purpose of providing a thorough understanding of the various exemplary embodiments of the present invention. However, it will be apparent to those skilled in the art that some aspects of the various exemplary embodiments of the present invention may be practiced without these specific details. In some instances, well-known structures and components are shown in block diagram form in order to avoid obscuring various examples of various embodiments.

Figure 1:
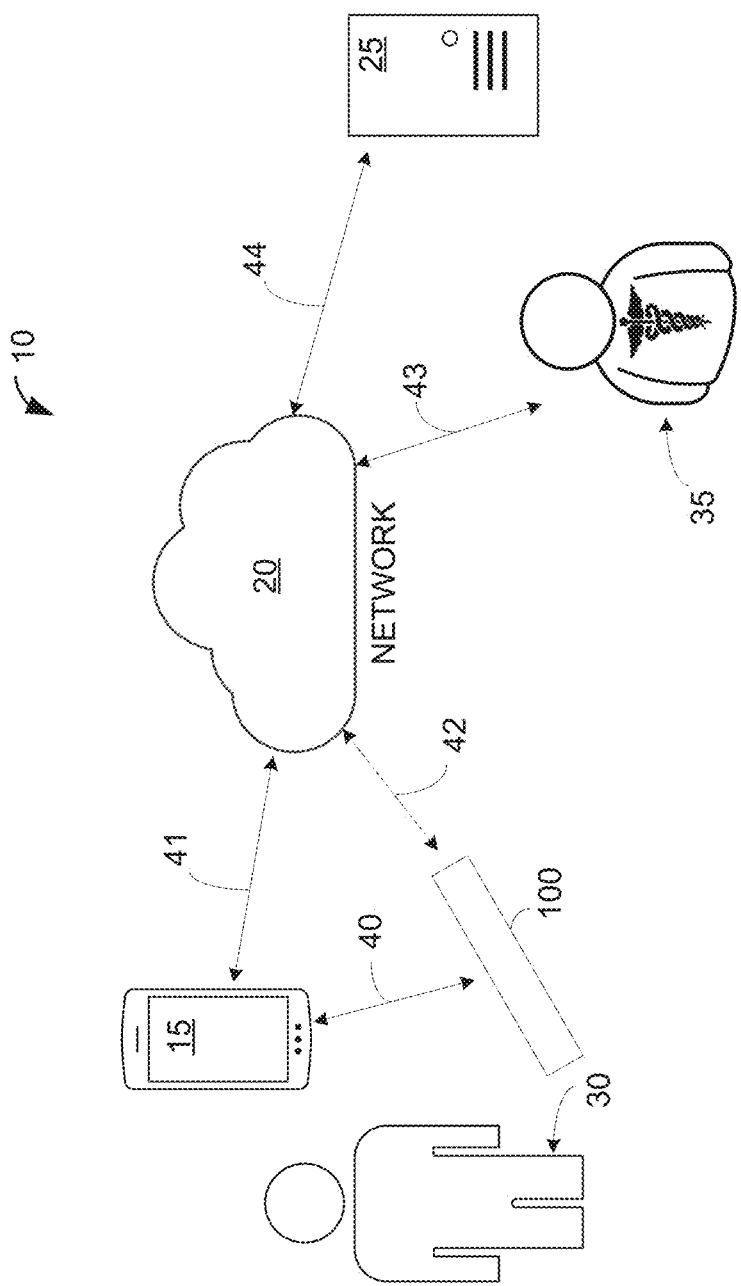
FIG. 1 illustrates an overview of an addiction cessation system, for example, a smoking or vaping cessation system ("cessation system").

This disclosure relates to addiction cessation systems, devices, and processes that can be used in an addiction cessation system which may implement a program to address and stop an addiction. In some implementations, the systems, devices, and methods are employed to help a user stop smoking or vaping. For ease of reference, as used herein "smoking" is used in reference to smoking and/or vaping. Reference to a "smoking cessation device," a "smoking cessation system," or "a method for smoking cessation," or similar phrases, refer to either, or both, a device, system, or a method that can be used to facilitate a user to stop smoking, or to stop vaping. For example, a device, system, or a method that can be implemented in a cloud-based (or server-based) system for helping a user quit smoking or vaping, such as illustrated in FIG. 1, and described in further details in the subsequent figures. Accordingly, in the non-limiting examples described herein, the cessation systems, devices, and processes can be implemented in a smoking cessation program, or a vaping cessation program, the systems, devices, and processes can also be used to address, and quit, many other types of addictions. For example, the systems, devices, and processes can be used in many types of an addiction quitting program that benefits from having an individually tailored program based on user physiological and psychological characteristics, administering mixtures of multiple substances to a user via an inhalation device, daily automatic monitoring of the user's progress in the quitting program, and providing nearly instantaneous feedback to the user throughout each day of the quitting program, as needed. Accordingly, although most of the examples herein may relate to a smoking cessation program or a vaping cessation program, the uses of the disclosed systems, devices, and processes are not limited to these applications. For ease of reference, "smoking" is used herein to refer to either and both smoking and vaping unless otherwise indicated explicitly or by the context of the disclosure, such that a "smoking cessation program" refers to a smoking and/or a vaping cessation program. In addition, the substance smoked is not limited to a tobacco product, but instead the applies to any substance or material that can be smoked, atomized, aerosolized, or sprayed, and inhaled by a user.

The difficulty of quitting smoking is well-known. The likelihood a smoker's attempt to quit smoking will be successful is greatly increased when both physiological and psychological aspects of smoking are addressed. To date, the physiological and psychological aspects of quitting smoking are generally addressed at least somewhat separately. Therefore, many smokers attempt to quit smoking or vaping using one or the other. Additionally, the lack of integration between the physiological and psychological aids also reduces the effectiveness of an attempt to quit smoking. In addition, during many, if not all, smoking cessation programs monitoring of the user's smoking behavior is based on user provided information and is not objectively collected, and there has been no way to accurately monitor and track the user's daily behavior. User provided information can be inconsistent and inaccurate at least for the reasons that as it may be unreliably collected and even falsely provided.

Figure 7A:
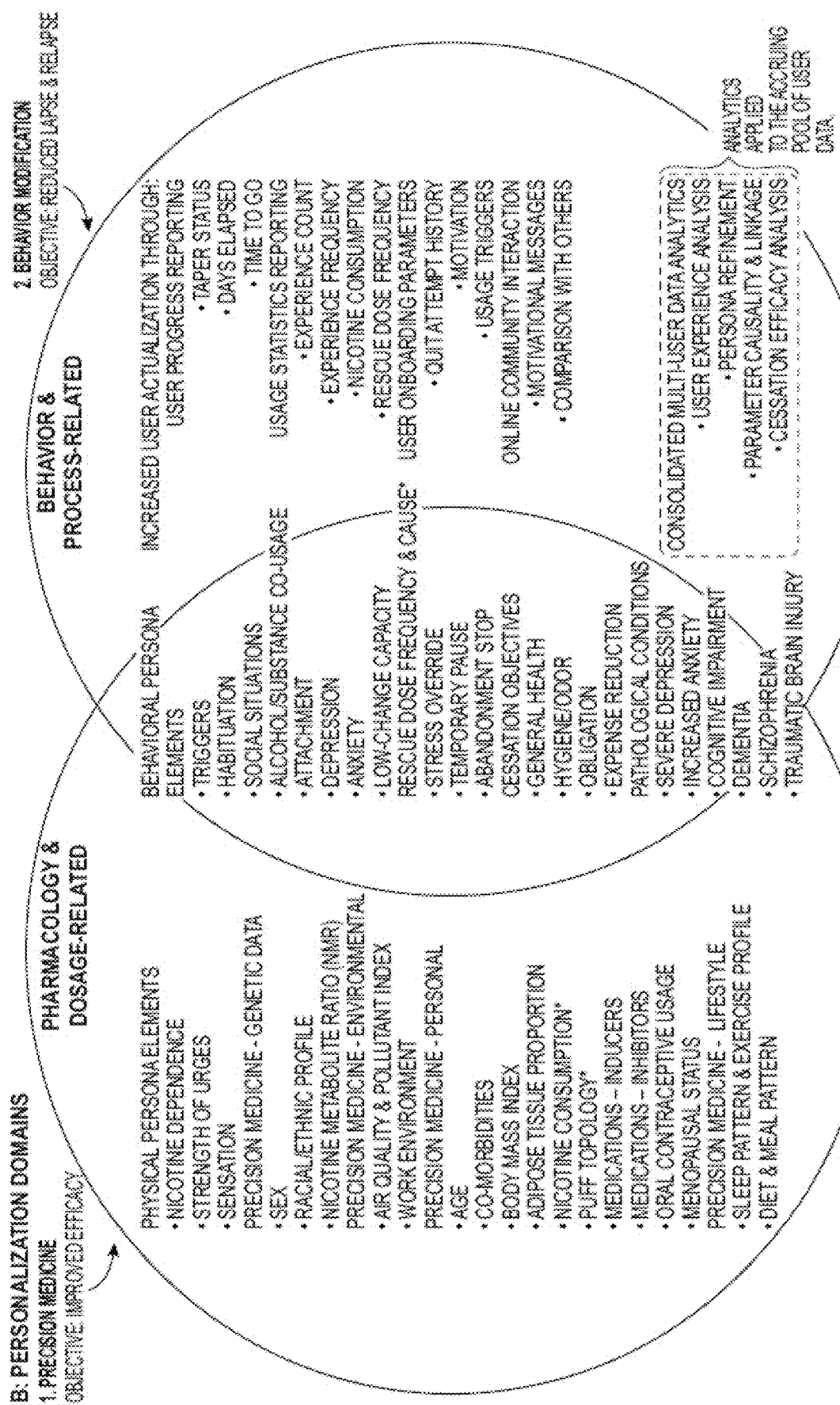
FIG. 7A is a diagram illustrating an example of intersecting personalization domains utilized by the smoking cessation system.

The systems, devices, and methods disclosed herein address these problems, and others. They advantageously can objectively monitor a user's activities, collecting accurate and detailed information of a user's use of a smoking cessation device as the user progresses through a cessation program, the collected information being relating to use characteristics of the cessation device that are impossible for a user to collect themselves. In the disclosed embodiments of a cessation program, is "onboarded" where a cessation program is individually generated based on user individual characteristics that may be genetic, determined from a user interview, and/or testing. For example, for smoking, one or more of nicotine dependence, strength of urges, perceived sensation of smoking, sex, race/ethnicity, nicotine metabolite rate (NMR), environmental (e.g., air quality, pollution index, work environment), age, co-morbidities, body mass index (BMI), adipose tissue proportion, nicotine consumption, puff topology, medications, oral contraceptives use, menopausal status, sleep pattern, exercise profile, and diet, nutrition, and meal pattern. These factors and others are illustrated in FIGS. 7A-7P, which disclose aspects of personalization of a cessation program, behavior modification objectives, and steps of the cessation process. For example, disclosing an exemplary smoking cessation process that includes on-boarding a user into the cessation program, cigarette taper, nicotine taper, placebo usage, and relapse protection (see, for example, FIG. 7Q).

Accordingly, a cessation system can include an individually tailored dynamic cessation program for a user. The program can be administered using a cessation system that includes a server-based system (e.g., cloud-based system), which is running a cessation application. The cessation system can also include a mobile device that communicates with the server-based system and provides information relating to the cessation program and the user's progress, to the user. The cessation system can also include a cessation device (an inhalation device) that administers an aerosol mixture to the user based on the cessation program. The cessation device includes a plurality of sensors relating to its use, and signals from the sensors are used to monitor the user's progress through the cessation program, and to dynamically tune the cessation program as needed. Information generated from the cessation device can be communicated to the mobile platform (e.g., via a Bluetooth link), used to provide information to the user, and also communicated to the server-system to be used in the cessation application. For example, a hardware processor in the cessation device may monitor and record the number of puffs of a cigarette, the duration of each puff, the total inhaled time, the amount of nicotine ingested, the flow rate, a density measure of the aerosol produced by each of three aerosolizers, a temperature measure of the aerosol produced by each of three aerosolizers, the aerosol mixture administered (based on three different substances), the ambient temperature, the ambient pressure, and other aspects.

The cessation systems described herein can include a cessation device that is configured to control an aerosolizer system having a plurality of aerosolizers. In some examples, the aerosolizer system includes two aerosolizers. In some examples, including examples illustrated in FIGS. 3A, 3B, 3C, and 4, an aerosolizer system includes three aerosolizers. In some examples, the aerosolizer system can include four or more aerosolizers. The cessation device is configured to control each aerosolizer separately such that the plurality of aerosolizers generate desired aerosol mixtures based on an individually tailored smoking cessation program, where the aerosol mixtures are dynamically changed based on the cessation program as a patient proceeds through the cessation program.

Although particular aspects various exemplary embodiments are described herein, numerous variations, combinations and permutations of these aspects fall within the scope of the disclosure. Although some benefits and advantages of certain aspects are mentioned, the scope of the disclosure is not intended to be limited to particular benefits, uses or objectives.

LIST OF CERTAIN COMPONENTS

For ease of reference, below is a list of certain components that are described and enumerated in this disclosure in reference to the above-listed figures of a cessation system. Other components not listed below may also be included in a cessation system. Any aspect of the devices illustrated in the list below, or included in the figures or description, whether or not named out separately herein, can form a portion of various embodiments of the invention and may provide basis for claim limitation relating to such aspects, with or without additional description. Certain enumerated components include:

10—cessation system
15—mobile device/smart phone/computer
20—network
25—server system (e.g., cloud-based server system)
30—user
35—advisor(s)/medical practitioner(s)
40—communication link between cessation device and mobile device
41—communication link between mobile device and network
42—optional communication link between cessation device and network
43—communication link between network and advisor(s)/medical practitioner(s)
44—communication link between server system and network
100—cessation device (inhalation & monitoring device and aerosolizer pod)
101—distal end of housing
102—housing
103—proximal end of housing
104—channel
105—opening in housing for receiving aerosolizer system
106—opening for receiving air
107—proximal end of channel
108—opening on proximal end of channel for providing air to aerosolizer system
109—cessation device or "pen" 110—aerosolizer driver
110—aerosolizer driver
111—electrical connection(s)
112—flow sensor
113—circuit
114—power source (e.g., battery)
116—rescue button
118—fingerprint sensor
119—carbon dioxide sensor/oxygen sensor
120—antenna
121—carbon dioxide sensor
122—distal end of channel
130—controller
140—cavity for receiving aerosolizer system 141—cessation device exhaust port
145—substance (in aerosolizer container)
150—aerosolizer system (pod)
151—distal end aerosolizer system
152—heating element
153—proximal end aerosolizer system
154—intake (opening) of aerosolizer
155—proximal end passage
156—passage
157—distal end of passage
158—temperature sensor
159—aerosolizer container
160—density sensor
161—aerosolizer (unit)
162—aerosol mixing chamber
163—pod ID chip
164—exhaust port (opening) of mixing chamber for providing aerosol mixture
165—case
166—walls of mixing chamber
167—mixing space (volume) in mixing chamber
167—charging connection to pen
168—case battery
169—charging port
170—mixing chamber intake opening
171—sensing port
405—ambient temperature sensor
407—ambient pressure sensor
410—flash memory
415—LEDs
420—Battery Manager
425—case data interface
430—case charge interface
465—pod ID chip interface
500—computer system
502—communication bus
504—hardware processor
506—non-transitory memory (component)
510—storage device (e.g., solid-state memory)
512—display
514—input controls
518—communication interface
601—puff data
602—usage
603—profile
604—data input
605—progress
606—output
607—cessation schedule
608—cessation application
801—on-boarding phase
802—cigarette taper phase
803—nicotine taper phase
804—placebo usage phase
805—software support phase Illustrative Examples of Smoking Cessation Systems Described below are illustrative examples of embodiments of systems and methods of a smoking cessation device, and methods for cessation of smoking. Other examples of such systems and methods for smoking cessation using some, or all, of the described technology, or additional technology with the described technology, are also possible.

FIG. 1 illustrates an example of a cessation system 10, according to some embodiments, showing examples of components and communication links that can exist between the components of an exemplary cessation system 10. In this example, the cessation system includes a server system 25, a cessation device 100 used by a user 30, and a computer/mobile platform ("mobile platform") 15. One or more advisors or medical practitioners 35 can also receive information relating to the cessation program and the user's progress in the cessation program, and provide input to the cessation program or to the user 30.

The components of the cessation system 10 can communicate via a network 20, and one or more of communication links, which include a communication link 40 between the cessation device 100 and the mobile platform 15, a communication link 41 between the mobile platform 15 and the network 20, a communication link 43 between the advisors 35 and network 20, and a communication link 44 between the server 25 and the network 20. One or more portions of the network 20 and communication links 40-44 can include a wired or wireless communication link, and can include Wi-Fi, Bluetooth, cellular, or any suitable communication link. The network 20 can be, for example the Internet, or another large area network (LAN), or a wide area network (WAN). In some examples, the cessation device 100 can include directly to the network 20 via a communication link 42 (e.g., a wireless communication link).

Figure 3A:
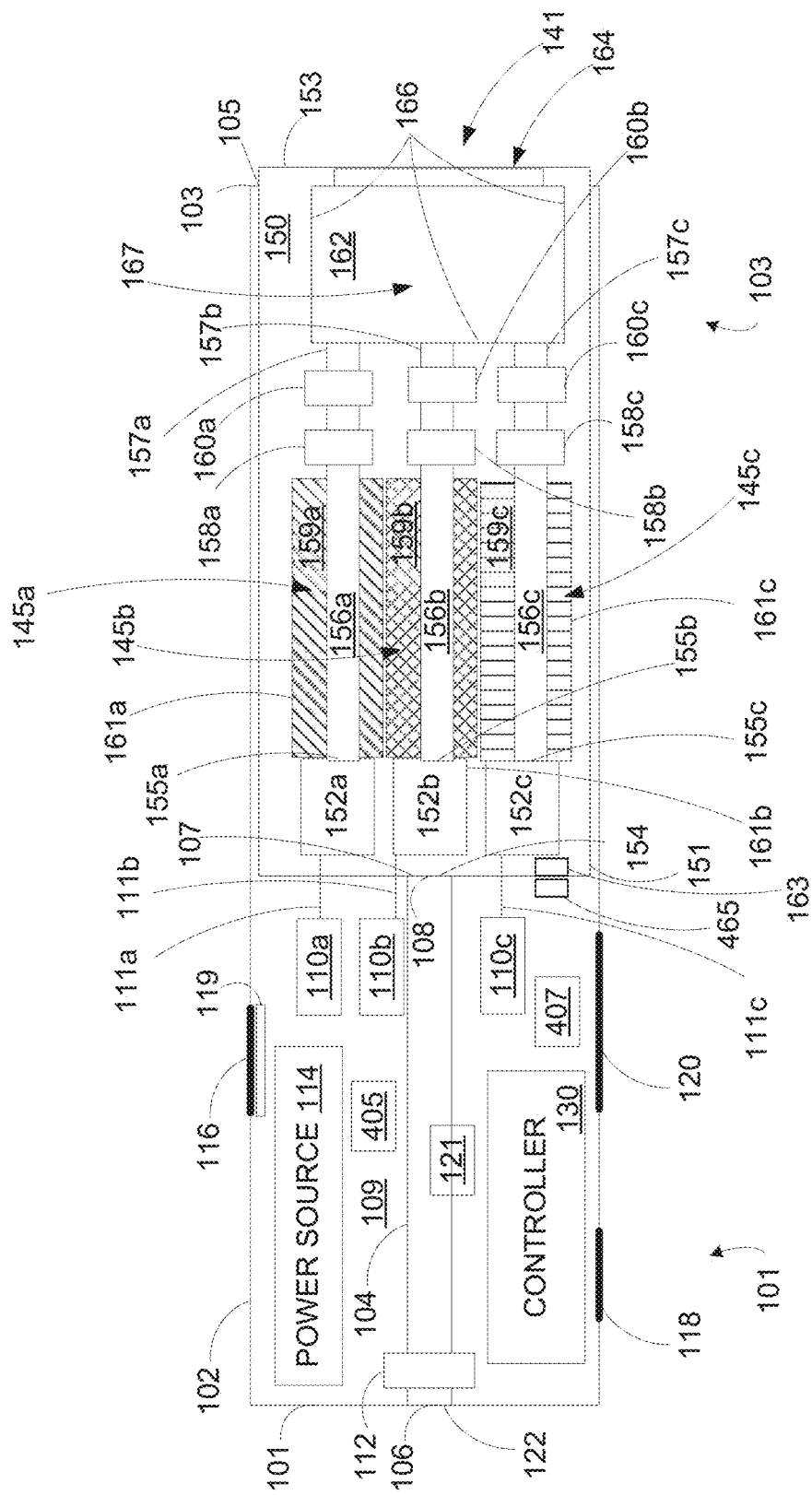
FIG. 3A is a schematic of an example of a cessation system, illustrating the aerosolizer system coupled to the housing.
Figure 3B:
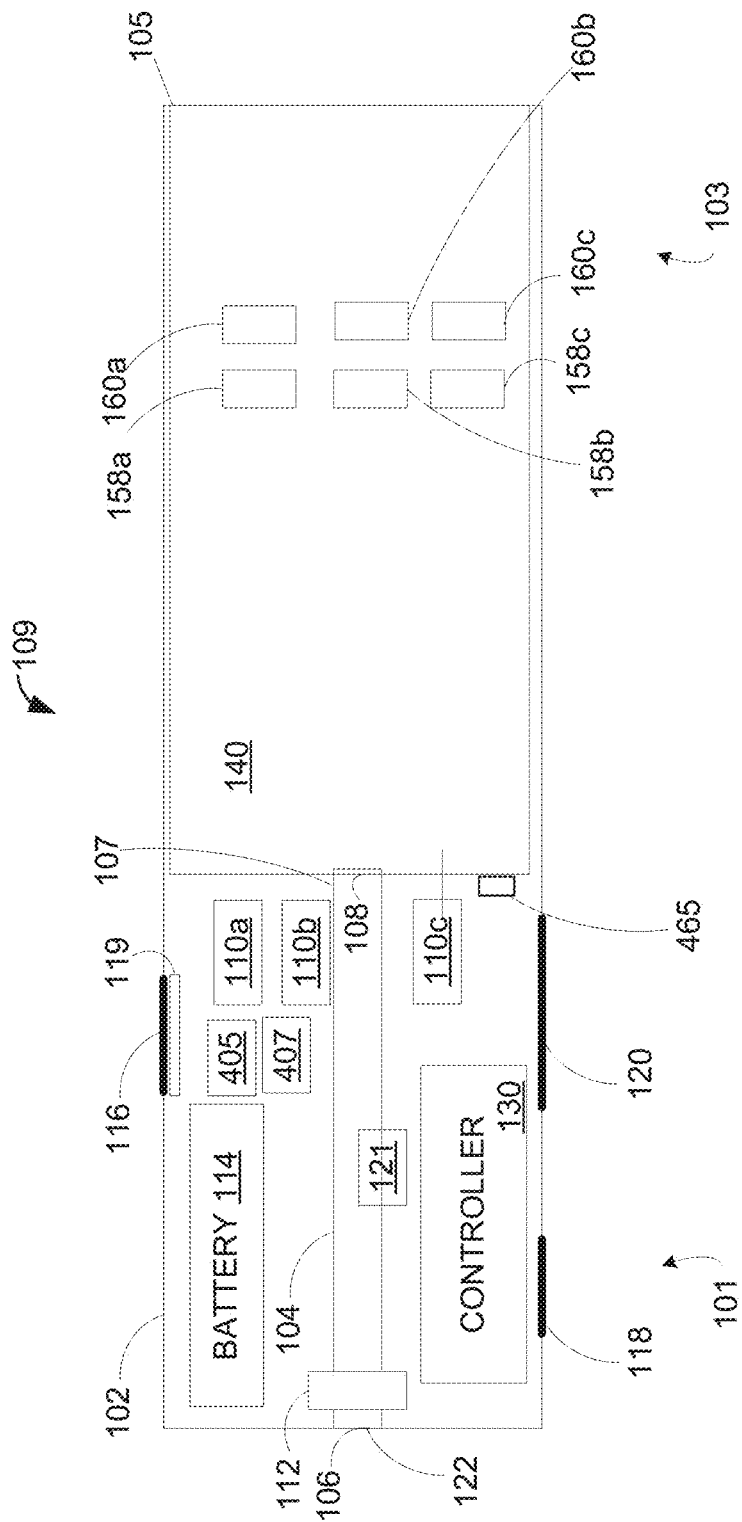
FIG. 3B is a schematic of the housing of the cessation system illustrated in FIG. 3A.
Figure 4:
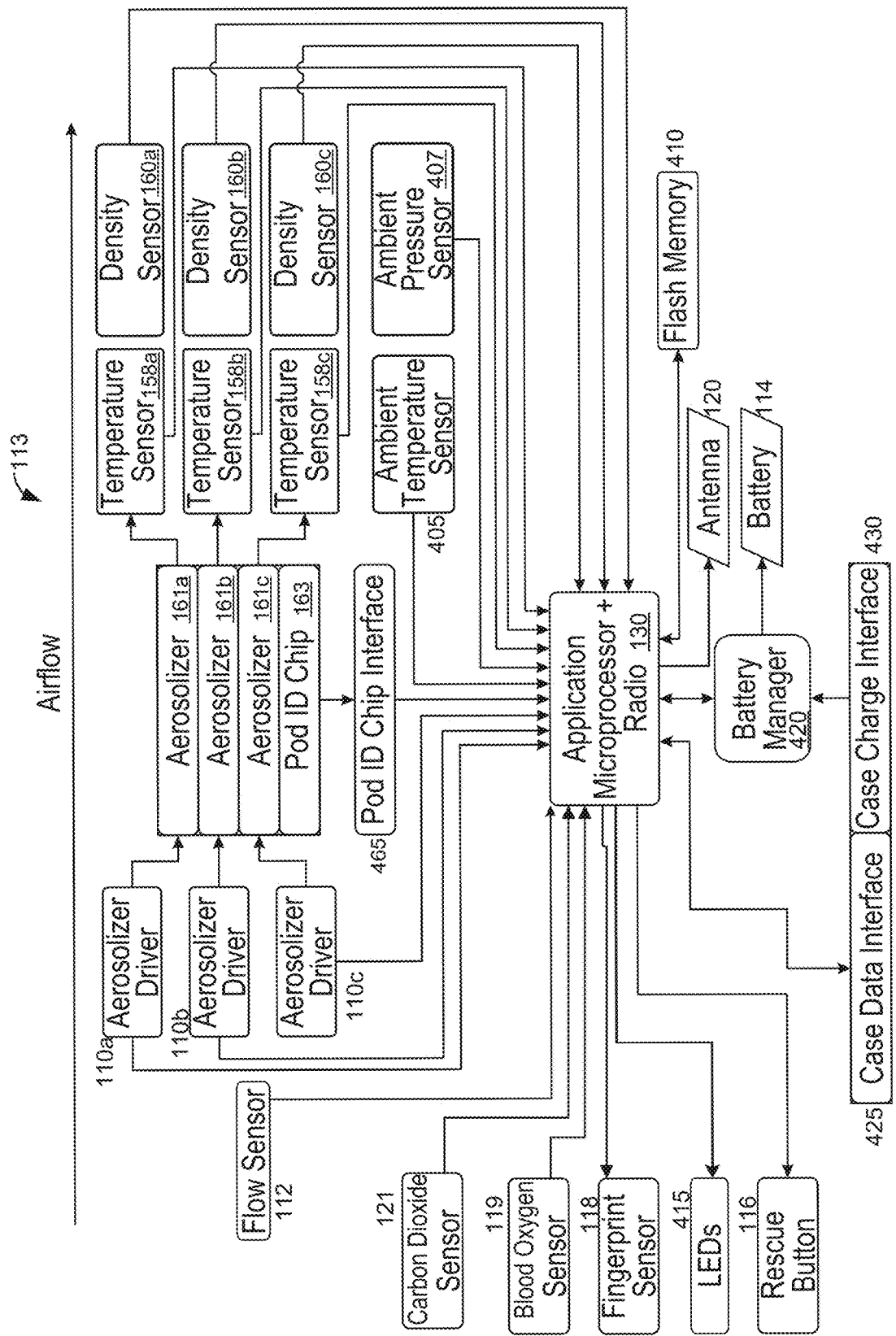
FIG. 4 is a schematic of an example of a controller that can be used in a cessation system, showing communication lines between a hardware processor and other components of the cessation system.

In this example, the server 25 is configured with a cessation program which is tailored to an individual user. As described below (for example in reference to FIGS. 7A-7Q) a user is "onboarded" and an individually tailored cessation program is generated using factors specific to the user (see, for example, FIGS. 7A, 7B-1, and 7B-2). The server 25 provides information to the mobile platform 15 to operate the cessation program, and the mobile platform 15 provides cessation program information to the cessation device 100, which may include software updates, revised cessation program information, and the like. During a cessation program, the use of the cessation device 100 is monitored by the cessation device 100 using one or more sensors. FIGS. 3A, 3B, and 4 illustrated examples of sensors that may be included on the cessation device 100. Information related to the cessation program can be communicated from the cessation device 100 to the mobile platform 15, and then to the server 25. The information received by the server 25 can be used by the server 25 to monitor and/or revise the cessation program. The information received by the sever 25 can also be used to provide reports to advisors 35. In addition, the information received by the server 25 for each user can may be used as data change overall parameters of the cessation program for other users. For example, information from hundreds, thousands, tens of thousands, or more, of users can be used to train a machine learning system to increase the efficiency and the effectivity of the cessation program for current users and/or new users.

The mobile platform 15 can provide cessation program information to the cessation device 100, including information which controls an aerosol mixture the cessation device 100 generates from a plurality of aerosolizers to dynamically provide desired aerosol mixtures as required by the cessation program. In some embodiments, the mobile platform 15 can run at least a part of the cessation program, for example, through an app running on the mobile platform 15. The mobile platform 15 includes a display, and provides certain cessation program information on various graphical user displays (GUI's) to the user 30 based on the received information, for example, information relating the user's progress, or encouraging information for the user to adhere to the cessation program. The mobile platform 15 also receives information from the cessation device 100 relating to the user's use of the device (including information from sensors on the cessation device 100), and can communicate some or all of the received information to the server 25. As indicated above, the mobile platform 15 can communicate changes/revisions of the cessation program and related information, including revisions to software or new software, to the cessation system 100, including information the mobile platform 15 receives from the server 25.

The cessation device 100 is an inhalation device used by the user 30 to help the user 30 stop smoking or vaping. The cessation device 100 is configured to be coupled to an aerosolizer pod 150 (FIG. 2) having a plurality of aerosolizers. An example of a cessation device 100 and an aerosolizer pod 150 having three aerosolizers is illustrated in FIGS. 3A-3C. The cessation device 100 can include structure and a variety of sensors and components that are used to monitor use of the cessation device and implement the cessation program including revisions to the cessation program when needed. In an example, a cessation device can include a housing having a distal end and a proximal end, a channel having an opening on a distal end for receiving air and an opening on a proximal end to communicate air to an aerosolizer pod coupled to the housing. The cessation device can also include an aperture on the proximal end of the housing configured to receive an aerosolizer pod therein. The housing can be configured to at least partially surround the aerosolizer pod when the aerosolizer pod in positioned in the housing. The cessation device can include a plurality of sensors, including one or more of a flow sensor positioned to sense air flowing through the channel, a first, second, and third density sensor for sensing density of aerosol generated by a first, second, and third aerosolizer (respectively), a first, second, and third temperature sensor configured to sense a temperature of aerosol generated by the first, second, and third aerosolizer (respectively), an ambient temperature sensor, an ambient pressure sensor, a fingerprint sensor, a carbon dioxide sensor, and/or an oxygen sensor. The cessation device 100 can also include a first, second, and third aerosolizer driver configured to electrically couple to the first, second, and third aerosolizer (respectively), a power source, and a controller circuit. In some embodiments, the cessation device includes components to control four or more aerosolizers. The controller circuit can include a hardware controller coupled to the flow sensor, the first, second and third density sensors, the first, second and third temperature sensors, the first, second, and third aerosolizer drivers, and a rescue button. The hardware controller can include a hardware processor and a non-transitory computer readable medium in communication with the hardware controller, the computer readable medium configured to store smoking cessation program information, and to store executable instructions that, when executed, configure the hardware controller to perform a smoking cessation program that includes receiving input signals from the flow sensor, the first, second, and third density sensors, the first, second, and third temperature sensors, and the rescue button, and individually controlling the three aerosolizer drivers to provide aerosolizer generation signals to control the first, second and third aerosolizers of the aerosolizer pod to generate an aerosol mixture based at least on the received input signals and the smoking cessation program information. These, and other components, are described in more detail below, for example, in FIGS. 2-5.

Figure 2:
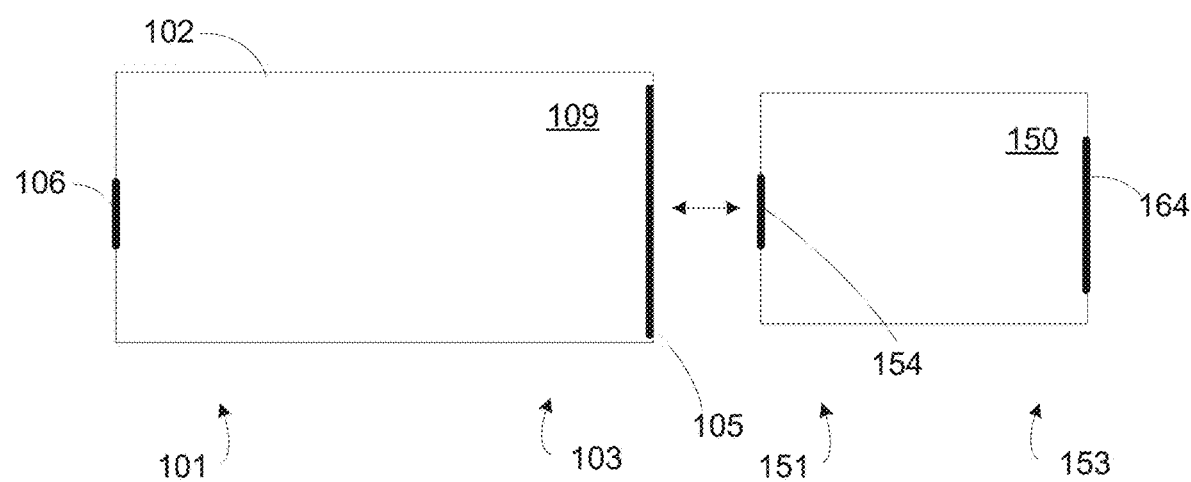
FIG. 2 is a schematic of an example of a cessation system that includes a housing and an aerosolizer system (or "aerosolizer pod") that can be removably coupled to the housing.
Figure 3C:
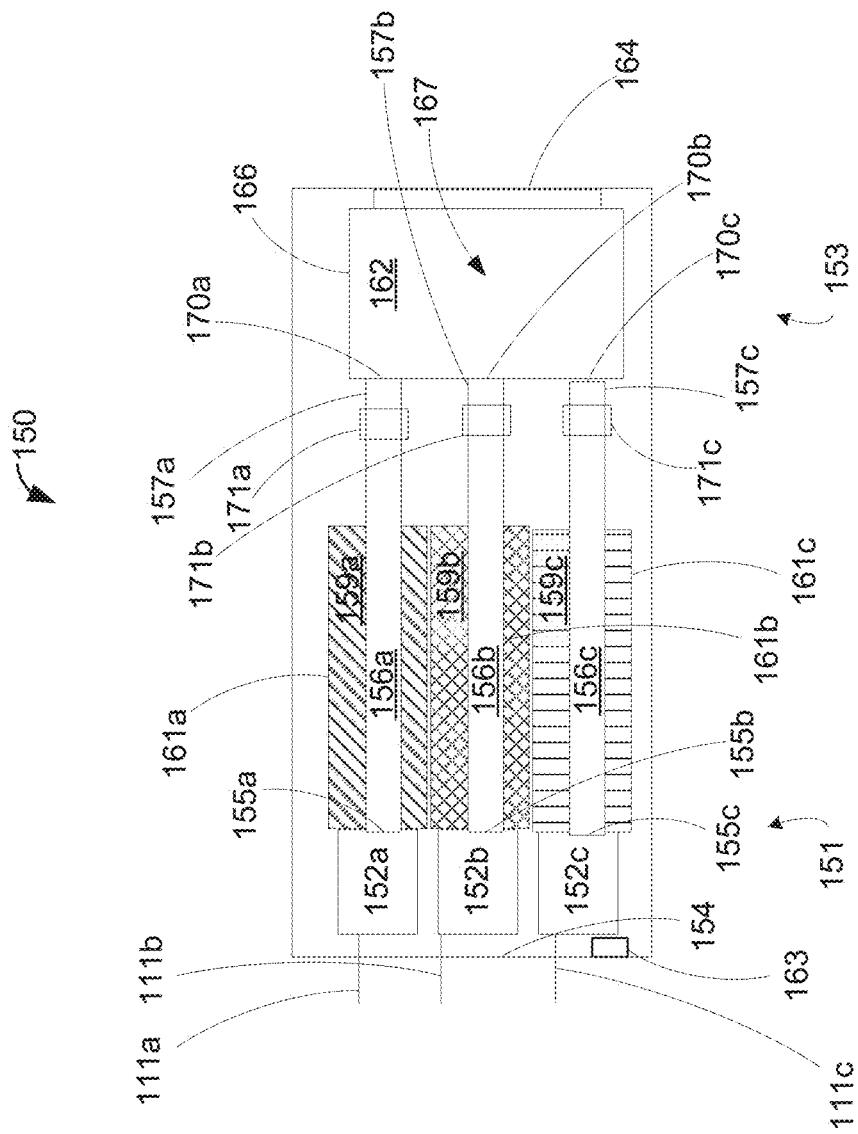
FIG. 3C is a schematic of the aerosolizer system of the cessation system illustrated in FIG. 3A.

FIG. 2 is a schematic of an example a cessation device 109 and an aerosolizer system (or "pod") 150 that can be used in the cessation system 10. As described in more detail in reference to FIG. 3, the cessation device 109 includes components to perform a cessation program and control multiple aerosolizers in the pod 150 to generate desired aerosol mixtures, which is then inhaled by a user. The pod 150 can be removably coupled to the cessation device 109. In this example, the pod 109 is at least partially inserted into the cessation device 109 to couple them together. Also in this example, when the pod 150 is coupled to the cessation device 109, the aerosolizer drivers in the cessation device electrically connect to corresponding aerosolizers in the pod 109. The aerosolizer drivers can independently and separately provide signals to each aerosolizer in the pod 109, and generate desired aerosol mixtures of the different substances in the multiple aerosolizers of the pod 150 in accordance with the cessation program.

The cessation device 109 includes a distal end 105 having an opening 106 for receiving ambient air into the cessation device 109. The cessation device 109 is configured with one or more air communication channels such that air received through the opening 106 is provided to the pod 150. The pod 109 also can includes one or more air communication channels to provide air to each aerosolizer in the pod 150. The cessation device 109 includes a second opening 105 in the housing 102 which is configured to receive the pod 150 such that at least a portion of the pod 150 is positioned within the housing 102 in his coupled to the housing 109. The pod 150 includes an opening 154 on a distal end 151 through which to receive air passing through the cessation device 109. The pod 150 further includes, on its distal end 153, an opening 164 for providing an aerosol mixture to a user. Examples of certain components that can be included in the cessation device 109 and the pod 150 are illustrated in FIGS. 3A-3C, 4, and 5.

Figure 3D:
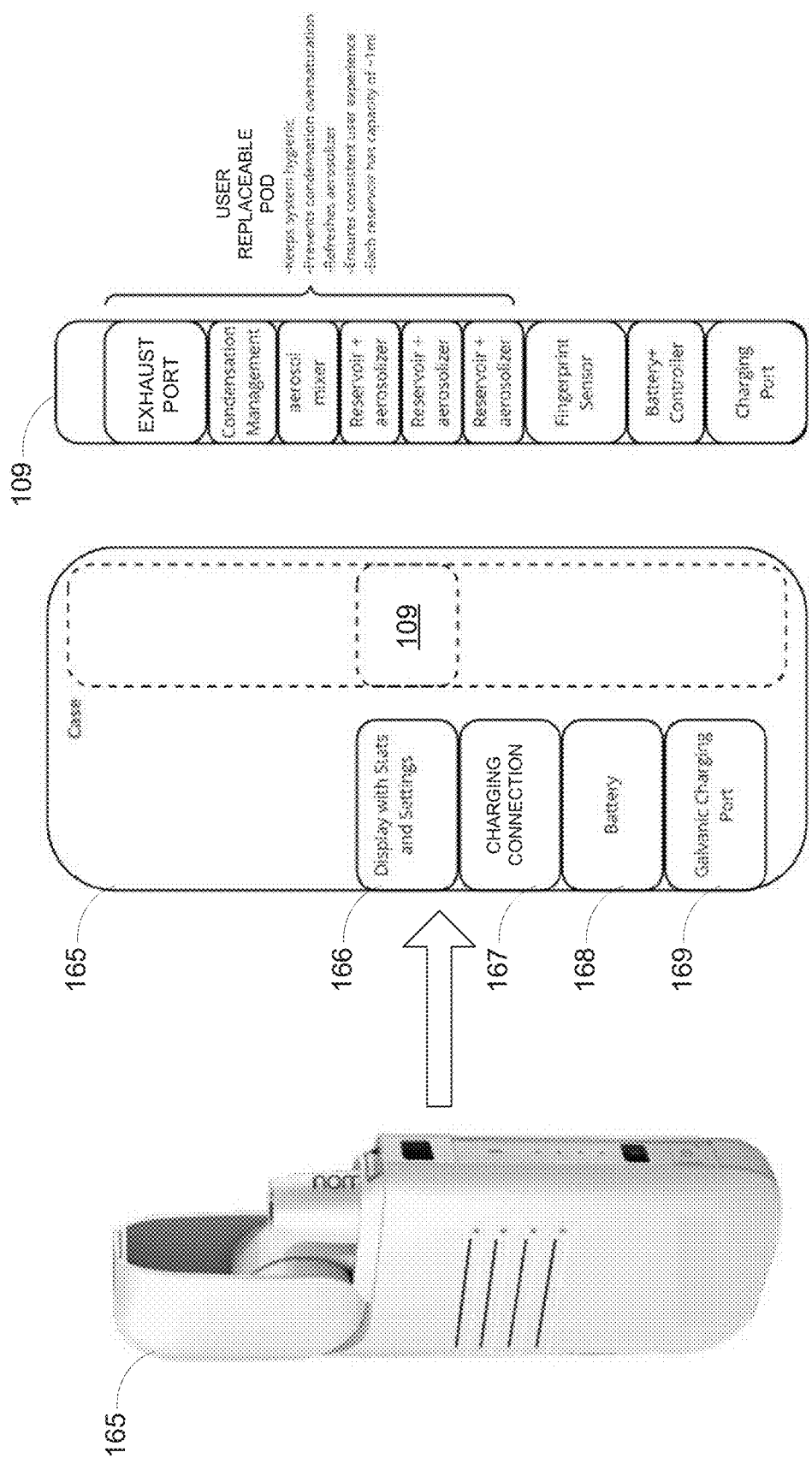
FIG. 3D is a schematic of the case and the cessation device containing the components illustrated in FIG. 3A.

An example of a cessation device 100 and an aerosolizer system (or "pod") 150 that can be coupled to the cessation device 100 and used in the cessation system 10 are illustrated in FIGS. 3A-3D. Specifically, FIG. 3A illustrates an example of the cessation device 100 with the pod 150 coupled to the cessation device 109. FIG. 3B further illustrates the cessation device 109 shown in FIG. 3A. FIG. 3C further illustrates the pod 150 of the shown in FIG. 3A. FIG. 3D illustrates a case 165 that can be used to house the cessation device 109 and pod 150. In various embodiments, the case 165 can include one or more additional components for facilitating use of the cessation device 109. Referring to FIG. 3A, in this example, the entire pod 150 is positioned within the housing 102 when the pod 150 is coupled to the cessation device 109. In other examples, a portion of the pod 150 may be coupled to the cessation device 150 and extend from the proximal end 103 of the cessation device 109. In this example, the pod 150 is coupled to the cessation device 109 such that it is in electrical communication with the cessation device 109 and in fluid communication with air flow into and through the housing 102 (e.g., through opening 106, through channel 104, and through opening 108).

A number of components and structures can be positioned within the housing 102 of the cessation device 109, for example but not limited to those illustrated in FIGS. 3A and 4. In this example, a channel 104 for providing ambient air to the pod 150, has a distal end 122 at the distal end 101 of the housing 102 and extends from the opening 106 towards a proximal end 107 of the channel to opening 108. When the pod 150 is in the housing 102, an intake 154 of the pod 150 is aligned with the opening 108 such that air is communicated through the channel to the pod 150. In other examples, instead of a single opening 106, the cessation device 109 may include one or more openings 106 and/or one or more channels 104 to receive air into the housing 102 and communicate the air to the pod 150. In some embodiments, the opening 106 may be located at a different portion of the housing 102 instead of at the distal end 101. In an example, the housing may include one or more openings 106 on a side surface of the housing 102 instead of, or in addition to, the distal end 101. In some embodiments, one or more openings 106 are located in a gap, or near a gap, between the housing 102 and the pod 150. The cessation device 109 also includes an opening 105 in the housing 102 on the proximal end 103 of the cessation device 109, the opening 105 structured to allow the pod 150 to be placed into the housing 102 through the opening 105. In this example, the cessation device 109 includes a cavity 140 which extends from the proximal end 103 of the housing 102 into the housing 102. The cavity 140 and walls of the housing 102 surrounding the cavity are structured to receive and hold the pod 150.

The cessation device 109 also includes a controller circuit 130 which is connected to a power source 114. The controller circuit 130 can include one of more hardware processors and non-transitory computer readable medium, for example, as described in reference to FIG. 5. The power source 114 can include, for example, a battery, capacitor, super-capacitors, or another energy storage medium, or a combination thereof. The power source 114 can be configured to provide electrical power to the pod 150 when the pod 150 is coupled into the cessation device 109. In some examples, the pod 150 also includes a power source. The controller circuit 130 is in communication with one or more sensors to receive information (e.g., signals) from the sensors that the controller circuit 130 uses to run a cessation program. For example, the cessation device 109 can include a flow sensor 112 which is positioned and configured to sense airflow into the cessation device 109 through the channel 104. The controller circuit 130 is connected to the flow sensor 112 and receives information indicative of the of air passing through the channel 104 from the flow sensor 112. Based on information from the flow sensor 112, the controller circuit 130 can determine information indicating the use of the cessation system by a user. For example, a "puff" (an inhalation of air/aerosol from the cessation system by a user) frequency, a puff duration, and/or a puff amount, can be determined by the controller circuit 130 based on information from the flow sensor 112. A puff profile can also be determined by the controller circuit 130 based on information from the flow sensor 112. The "puff profile" refers to how the changes during the duration of the puff. For example, whether the profile (e.g., airflow as a function of time) of the puff is a square wave, trapezoidal-shaped, sinusoidal-shaped, and the like). The determined puff frequency, puff duration, puff amount, and/or the puff profile can be used by the cessation program to dynamically tailor the cessation program to a particular user's needs. Any signals/information the controller circuit 130 receives can be communicated one or more of the mobile platform 15 and the server 25, and used to monitor the user's progress in the cessation program, and used to modify the cessation program.

In this example, the cessation device 109 is configured to be used with a pod 150 that has three aerosolizer units ("aerosolizers") 161, as shown in the example in FIG. 3C. Each aerosolizer 161a-c can generate an aerosol from a substance contained in the pod 150. In this example, each aerosolizer 161a-c includes a heating element 152a-c (e.g., a resistive heating element) that can be controlled by the controller circuit 130 via the aerosolizer drivers 110aic to produce aerosol in accordance with the cessation program. The aerosol is communicated via passages 156A-c and enters the mixing chamber 162 through the mixing chamber intake openings 170a-c (FIG. 3C), where it forms an aerosol mixture which can be inhaled by a user. Each aerosolizer driver 110a-c can interact with a corresponding aerosolizer 161a-c to cause it to produce some or all of the aerosol mixture such that the aerosol mixture can include any proportion of a plurality of substances in the aerosolizers. In some embodiments, a temperature value is determined by the controller circuit 130 for each aerosolizer 161 by using the heating element 152 as a temperature sensor. For example, by sensing a change in a resistance (or impedance) value of the heating element as the temperature of the heating element 152 increases and correlating the resistance value to a temperature. Other embodiments may sense the temperature of an aerosolizer in different ways. For example, in some embodiments, the cessation device 109 can include temperature sensors 158a-c (shown in dashed lines) that are configured to sense the temperature of aerosol generated by the three aerosolizers 161a-c of the pod 150. The temperature sensors 158a-c can be positioned in the cessation device 109 such that when the pod 150 is coupled to the cessation device 109, each temperature sensor 158a-c is adjacent to one of the passages 156a-c that communicate aerosol from heating elements 152a-c to the mixing chamber 162 of the pod 150. The cessation device 109 can also include density sensors 160a-c that are configured to sense the density of aerosol generated by the three aerosolizers 161 of the pod 150. The density sensors 160a-c can be positioned on the cessation device 109 such that when the pod 150 is coupled to the cessation device 109, each density sensor 160a-c is positioned adjacent to one of the passages 156a-c that communicate aerosol from heating elements 152a-c of the pod 150 to the mixing chamber 162 of the pod 150. In some embodiments, the density sensors 160a-c can be optical sensors.

The cessation device 109 can also include a fingerprint sensor 118 which is connected to the controller circuit 130 and is used to sense a user's fingerprint to unlock the cessation device 109. In addition, the cessation device 109 can include an ambient temperature sensor 405 in ambient pressure sensor 407, in the controller circuit 130 can be configured to use information from the ambient temperature sensor 405 in the ambient pressure sensor 407 to control the cessation program provided to the user. For example, to control the aerosol mixture generated by pod 150 based at least in part on the ambient temperature and/or the ambient pressure.

In some examples, the cessation device 109 optionally also includes a carbon dioxide sensor 121 that is coupled to the controller circuit 130 and provides a signal to the controller circuit 130 indicative of an amount of carbon dioxide. The cessation device 109 can also include a control (e.g., a button, or fingerprint sensor 116) to activate the carbon dioxide sensor 121. In operation, after activating the sensor, a user exhales into the opening 106 to provide a flow of air to the carbon dioxide sensor 121 which provides a signal to the controller circuit 130. The information from the carbon dioxide sensor 121 can be used to determine a carbon dioxide level of the user and used in the cessation program, for example, to modify the cessation program.

In some examples, the cessation device 109 optionally also includes a blood oxygen sensor 119 that is coupled to the controller circuit 130 and provides a signal to the controller circuit 130 indicative of an amount of oxygen in the blood. In an example, the blood oxygen sensor 119 can be a pulse oximetry sensor. In some examples, the blood oxygen sensor 119 can be incorporated into the fingerprint sensor 116. In some embodiments, the blood oxygen sensor 119 can be separate from the fingerprint sensor 116.

The cessation device 109 can also include a pod ID chip interface 465 positioned near the cavity 140 that receives the pod 150. A pod 150 configured to be used with the cessation device 109 can include a pod ID chip 163 that is positioned on a portion of the pod 150 such that when the pod 150 placed into the cessation device 109, the pod ID chip interface 465 aligns with pod ID chip 163 to the extent that information may be communicated from the pod ID chip 163 to the pod ID chip interface 465 to communicate information relating to the configuration of the pod 150 to the cessation device 109. In an example, the information can relate to one or more of the substances in the aerosolizer's of the pod 109 (e.g., type of substance, amount of substance left). In another example, the information can relate to a pod ID which the cessation device 109 can compare to stored data to determine information relating to the pod 109 (e.g., information related to the aerosolizers 152) with the cessation device may use to properly provide desired aerosol mixture to a user.

The cessation device 109 also includes a "rescue" button 116 which can be activated to provide a user additional nicotine dose, in accordance with the cessation program. The controller circuit 130 saves information relating to the use of the rescue button 116. In some examples, the rescue button use information can be used by the cessation device 109 to modify the cessation program. In some examples, the rescue button use information is communicated by the cessation device 109 to the mobile platform 15 and/or the server 25, and used to track the user's progress in the cessation program and/or modify the cessation program. Modifications made to the cessation program can be downloaded to the cessation device 109 from the mobile platform 15. The cessation device 109 can include one or more other features, for example, an antenna 120, and communication circuitry to allow the cessation device 109 to communicate a smart phone 15 or to another computer device over a network (as illustrated in FIG. 1). Certain features of the controller circuit 130, or that are in communication with the controller circuit 130, are further illustrated in FIGS. 4 and 5.

Figure 5:
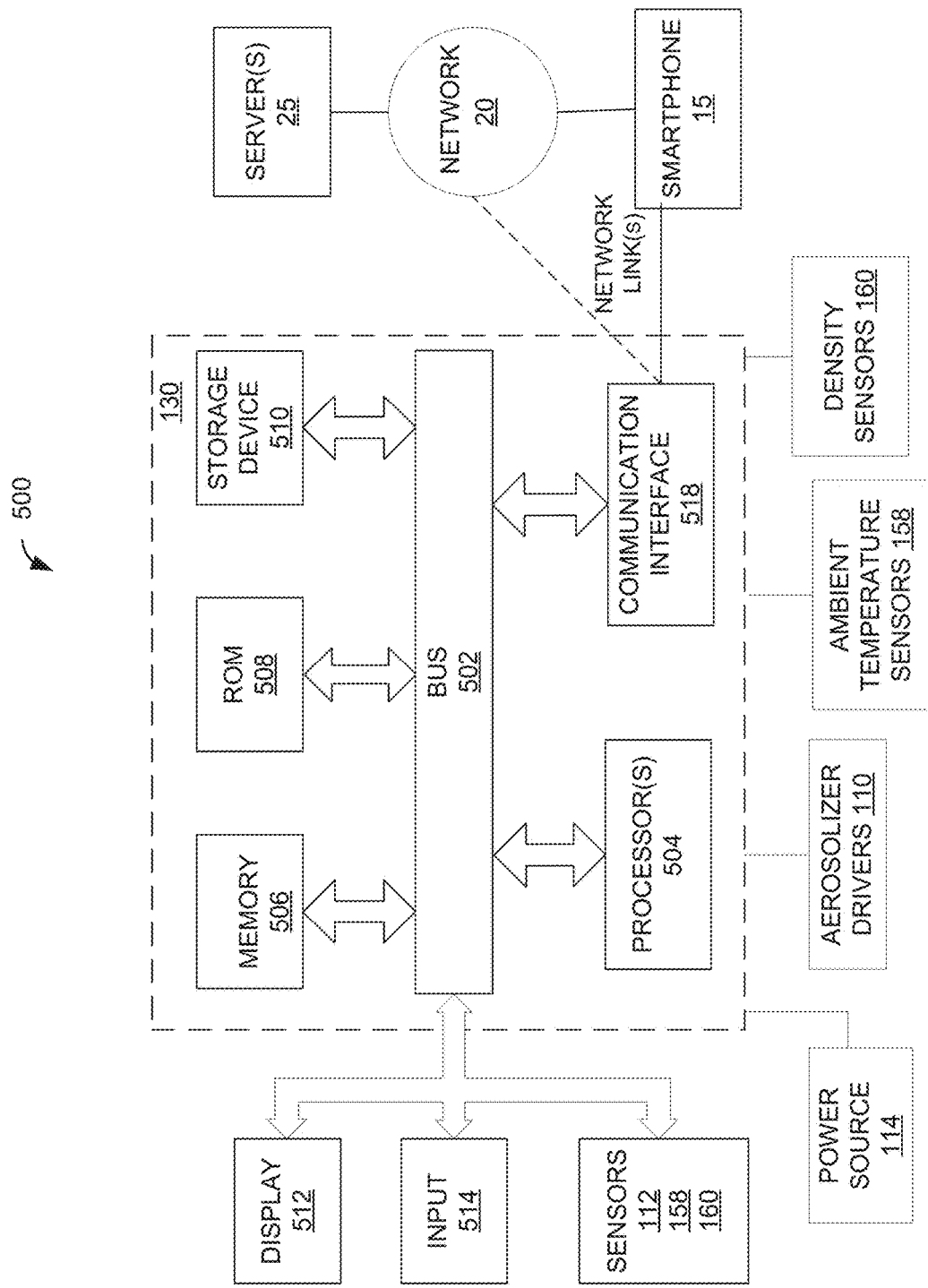
FIG. 5 is an example of a computer system that may be used to implement the functionality described herein.

As described in further detail in FIG. 5, the controller circuit 130 includes one or more hardware processors 504 that is in communication with at least one non-transitory memory component 506, 508 that includes executable instructions that figure the processor to run a smoking or vaping cessation program. The cessation device 109 includes a aerosolizer driver 110a-c for each of the aerosolizers 161 in the pod 150. The controller circuit 130 is connected to the aerosolizer drivers 110a-c and controls the aerosolizer driver 110a-c to operate respective aerosolizers 161a-c to generate aerosol such that a desired aerosol mixture reduced by the aerosolizer system provided to a user, as prescribed by the cessation program. For example, the controller circuit 130 can control the aerosolizers 161a-c, via the aerosolizer drivers 110a-c, to each generate a certain amount of aerosol from a substance (a fluidic mixture of nicotine) that in each aerosolizer 161a-c, such that the aerosol from each of the aerosolizers 161a-c is combined in the aerosol mixing chamber 162 of the pod 150 forming a desired aerosol mixture is provided to a user. The controller circuit 130 can also control the aerosolizers 161a-c, via the aerosolizer drivers 110a-c, to affect the aerosol droplet size (ADS) in the aerosol generated by each of the aerosolizers 161a-c. In some embodiments, the aerosol droplet diameters will be less than or equal to 20 μm. In some embodiments, the aerosol droplet diameters will be less than or equal to 10 μm. In some embodiments, the aerosol droplet diameters will be less than 1 μm or 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, or 20 μm, plus or minus 0.5 μm. In some embodiments, the aerosol droplet diameters will be less than or equal to 1 μm or in the range of greater than 5 μm to less than or equal to 10 μm (i.e., 5 μm<diameter≤10 m).

As illustrated in the example FIG. 3C, the pod 150 includes three aerosolizers 161 161a-c. Electrical connections 111a-c are each connected to one of the aerosolizers 161a-c, and can provide electrical power and/or control information to the aerosolizers 161a-c. When the pod 150 is coupled to the cessation device 109, the electrical connections 111a-c are coupled to the aerosolizer drivers 110a-c, respectively. Each aerosolizer 161 includes a heating element 152, a container 159 that is configured to hold a substance (e.g., a fluid containing nicotine), and a passage 156, each passage having a distal end 155 and a proximal end 157. The passage provides a flowpath for aerosol generated by the heating element 152 to flow to the mixing chamber 162. The mixing chamber 162 includes walls 166 enclose a mixing space 167. In the mixing chamber 162, the aerosol generated by each of the aerosolizers mixes together and forms an aerosol mixture, which a user can inhale through opening 164. In some embodiments, the pod 150 includes one or more power sources that can provide electrical power to the heating elements 152 or other electrical components of the pod 150. The controller circuit 130 can control the aerosolizer system to generate an aerosol mixture of a certain total nicotine concentration by controlling the aerosol generated by each of the aerosolizers for a cessation program.

Control of the aerosolizes can be based on the cessation program and based on inputs received from one or more of the sensors. Nicotine in e-liquids can exist in two forms— free base (meaning free from protons) and monoprotonated (meaning has one proton, also called a "salt"). There is a correlation between the pH level of the liquid and the ratio between the two forms. A common way to control the pH levels (and free base ratio) in the liquid is by using an organic acid in certain amounts to adjust the pH. In some embodiments, the total nicotine concentration delivered in the aerosol can range from 0 to 58 mg/mL. This total concentration is the sum of monoprotonated nicotine concentration, [NicH$^+$], and free-base nicotine concentration [Nic]. Note that nicotine can also exist in a di-protonated state, but this is practically never reached in tobacco aerosols because conditions in the aerosol droplets are not sufficiently acidic.

The free nicotine ratio ("FNR") can be calculated as:

$$FNR=[Nic]/([Nic]+[NicH^+])$$

$$FNR=1/(1+10^{-PH}/K_a)$$

where $K_a$ is the acidity constant for NicH$^+$ which is 8.01. So given a target FNR, the controller circuit 130 (e.g., firmware in the a hardware processor of the controller circuit 130) may calculate the required pH, and the microfluidics mix the high and low pH solutions (which contain exactly the same total nicotine concentration) to achieve this target pH thereby ensuring that the FNR is the value required.

As illustrated in FIG. 3D, the cessation device 109 (which may sometimes be referred to as a "pen") can be stored and charged within a portable charging case 165. The case 165 includes a screen 166 for the user to observe both statistics and settings to which the system is set. The case 165 houses and is powered by a rechargeable case battery 168 which can be accessed via a galvanic charging port 169 located on the case 165 shell. This charging port 169 can receive a mating plug connector to charge the case battery 168. When the cessation device 109 is not in use, it can be stored in a cavity within the case 165. The pen' power source 114 can wirelessly recharge from the battery within the case.

FIG. 4 is a schematic of an example of a circuit 113 that can be used in a cessation system, for example, the cessation system illustrated in FIGS. 1 and 3A. showing communication lines between a controller circuit 130 and other components of the cessation system, The controller circuit 130 can include one or more hardware processors 504 as illustrated in FIG. 5. In this schematic, the airflow is from left to right such that intake of air is sensed by the flow sensor 112 and is received by the aerosolizers 161. The aerosolizers 161 generate aerosol in the airflow, and the airflow then passes past 158 and density sensor 160, and then is taken into f100. FIG. 4 illustrates many components that are illustrated in FIG. 3A-3C. FIG. 4 also illustrates some additional components. For example, flash memory 410 is in communication with the controller circuit 130. The controller circuit 130 this example includes a transceiver or other communication circuitry that is coupled to an antenna 120 which allows cessation system 100 to communicate with a smart phone or to another device or a network. As illustrated in FIG. 4, the circuit 113 can also include a pod ID chip interface 465 (or aerosolizer chip interface) which, when the pod 150 is coupled to the cessation device 109, is in communication with a pod ID chip 163 of the pod 150 for providing signals (e.g., control signals) to the aerosolizer system and/or receiving information from the pod 150. The circuit 113 also include the case data interface 425 which is in communication the controller circuit 130, and a case charge interface 430 which is in communication with a battery manager for 420 which manages power provided to the controller circuit 130 into a power source (e.g., battery) 114 to, for example, manage the charging of the battery 114.

FIG. 5 is an example of a computer system 500 that may be used to implement the functionality described herein for a cessation system. In some embodiments, the computer system 500 can be characterized as including all electrical and electronic components of a cessation system. In some embodiments, the computer system 500 can be characterized as being the network cessation system illustrated in FIG. 1. In some embodiments, the computer system 500 can be characterized as including the controller circuit 130, where electrical and electronic components of a cessation system, as well as other computer systems, can be in communication with the controller circuit 130. In this particular example, the computer system 500 is described broadly as including the controller circuit 130 and other components are in communication with the controller circuit 130. However, nothing in this description is intended to limit the computer system 500 to be interpreted as referring to only the controller circuit 130 and its components.

The controller circuit 130 can include a bus 502 or other communication mechanism for communicating information between components of a cessation system, and a hardware processor, or multiple processors, 504 coupled with bus 502 for processing information. Hardware processor(s) 504 may be, for example, one or more general purpose microprocessors. The hardware processor(s) 504 include non-transitory memory 505. In some examples, the functionality the components illustrated in the controller circuit 130 can be implemented in a single chip (e.g., an ASIC) and the classification policy is stored in memory and/or in circuitry, for example, memory 505.

Computer system 500 also includes a main memory 506, such as a random access memory (RAM), cache and/or other dynamic storage devices, coupled to bus 502 for storing information and instructions to be executed by processor 504. Main memory 506 also may be used for storing temporary variables or other intermediate information during execution of instructions to be executed by processor 504. Such instructions, when stored in storage media accessible to processor 504, including on memory 505 integrated on a processor chip, render computer system 500 into a special-purpose machine that is customized to perform the operations specified in the instructions for a smoking or cessation program. Computer system 500 further includes a read only memory (ROM) 508 or other static storage device coupled to bus 502 for storing static information and instructions for processor 504. A storage device 510, such as a magnetic disk, optical disk, or USB thumb drive (Flash drive), etc., is provided and coupled to bus 502 for storing information and instructions.

Computer system 500 may be coupled via bus 502 to a display 512, such as a LCD or liquid crystal display, and which may include a touchscreen, for displaying information to a network operator. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512 by a network operator.

Computing system 500 may include a user interface module to implement a GUI that may be stored in a mass storage device as computer executable program instructions that are executed by the computing device(s). Computer system 500 may, as described below, implement the techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor(s) 504 executing one or more sequences of one or more computer readable program instructions contained in main memory 506. Such instructions may be read into main memory 506 from another storage medium, such as storage device 510. Execution of the sequences of instructions contained in main memory 506 causes processor(s) 504 to perform the process steps described herein. In alternative embodiments, hard-wired circuitry may be used in place of or in combination with software instructions.

Various forms of computer readable storage media may be involved in carrying one or more sequences of one or more computer readable program instructions to processor 504 for execution. The instructions can be for operating a cessation program using a mobile platform 15 and/or a cessation device 100. For example, the instructions may initially be carried on a magnetic disk or solid state drive of a remote computer (for example, server 25). The remote computer can load the instructions into its dynamic memory and send the instructions over a network. A transceiver in the computer system 500 and place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a network 20. For example, communication interface 518 may be an integrated services digital network (ISDN) card, cable modem, satellite modem, or a modem to provide a data communication connection to a corresponding type of telephone line. As another example, communication interface 518 may be a local area network (LAN) card to provide a data communication connection to a compatible LAN (or WAN component to communicated with a WAN). Wireless links may also be implemented. In any such implementation, communication interface 518 sends and receives electrical, electromagnetic or optical signals that carry digital data streams representing various types of information.

Network links typically provides data communication through one or more networks to other data devices. For example, the network link may provide a connection through a smartphone 15 to a server 25 via network 20. Computer system 500 can send messages and receive data, including program code, through the network(s), network links and communication interface 518. In an Internet example, a server 25 might transmit a requested code for an application program through network 20 and communication interface 518. The received code may be executed by processor 504 as it is received, and/or stored in storage device 510, or other non-volatile storage for later execution.

In various embodiments certain functionality may be accessible by a user through a web-based viewer (such as a web browser), or other suitable software program), and the user can install a predetermined classification policy, or update a predetermined classification policy, using these means. In such implementations, the user interface may be generated by a server computing system and transmitted to a web browser of the user (e.g., running on the user's computing system 500). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Figure 6A:
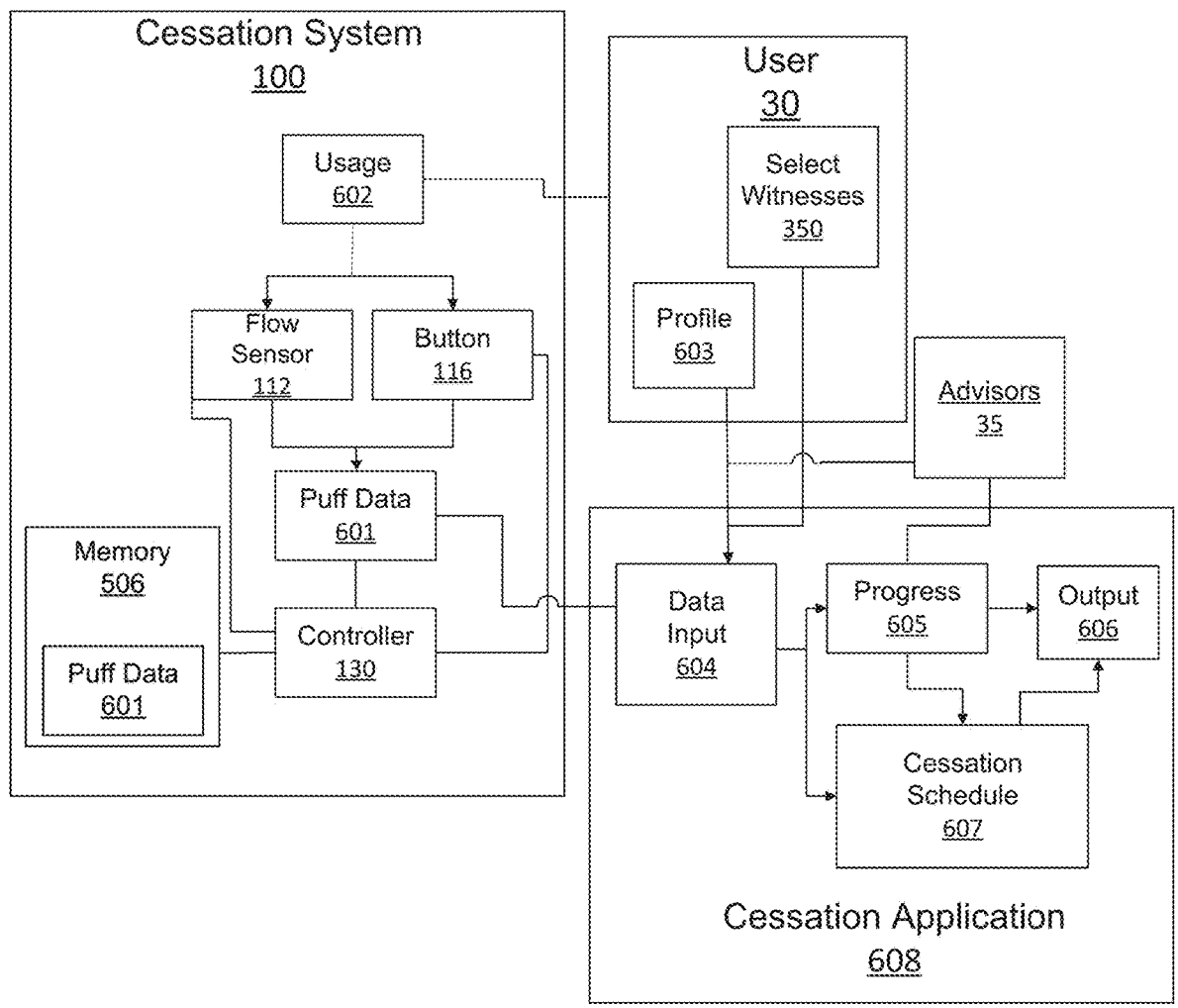
FIG. 6A is a diagram of a system for developing and implementing a smoking cessation program, according to one embodiment.

FIG. 6A is a diagram demonstrating an embodiment of the data flow logic of a smoking cessation system in accordance with the present disclosure. A new user 30 seeking to quit smoking may sign up for a cessation application 608. Upon signing up, the user 30 may be prompted to enter their profile 603 into the cessation application 608. The profile 603 includes characteristics that are relevant to nicotine withdrawal. This may include age, sex, height, weight, smoking history, including the number of cigarettes per day, the time of day of usage, biological co-factors, psychosocial co-factors, clinical co-factors, and any other relevant characteristics. For example, the application 608 may request the number of cigarettes smoked per day, the brand of cigarettes, whether the user 30 smokes e-cigarettes. If the user 30 indicates through the interface that they smoke e-cigarettes, the application 608 may additionally request the user provide how long each cartridge is used and the amount of nicotine per cartridge.

Once the initial data has been entered, the application 608 may determine an optimal cessation schedule 607 based on the user's 30 individual profile 603. That schedule may then be output 606 to the user 30. The output 606 may be in the form of a chart or table or other indication of the amount of cigarettes or puffs recommended for a user 30 for a particular period of time. This may include the number of cigarettes recommended for the day, week, or month, with options to display different time periods. Additionally, the user 30 may be given different options to select the pace of withdrawal from different recommended paces, some being a much faster drop from nicotine use.

The user 30 may seek help from outside advisors 35, like a physician, to measure or calculate the information required for the profile 603. The advisor 35 may also play a role in monitoring the progress 605 of the cessation application 608 which could lead to changes in the program over use.

The cessation system 100 receives data from the cessation application 608 to deliver the intended dose to the user 30. The cessation system 100 also stores puff data 601, which may include puff duration, puff interval, and/or puff volume, in memory 506, to send via the controller circuit 130 back to the cessation application 608. This puff data 601 may be monitored by the user 30 or the advisor 35 to facilitate in making any adjustments to the cessation schedule 607.

FIG. 6B is a flowchart illustrating an example of a cessation process 600, according to one embodiment. In an example, the cessation process 600 is for helping a user quit smoking. In another example, the cessation process 600 is for helping a user to quit vaping. In another example, the cessation process 600 is for helping a user to quit and addictive behavior. At block 605, the process 600 operates the cessation program on a handheld cessation system. In one example, the handheld cessation system is the cessation system 100 illustrated in FIG. 3A. At block 610, the process 600 controls the aerosol generated by each of three or more aerosolizers in the cessation system, based on the cessation program, to form an aerosol mixture. The aerosol mixture can then be inhaled by a user.

FIG. 6C is a flowchart illustrating another example of a smoking cessation process 700, according to one embodiment. At block 705 the process 700 provides a smoking cessation system having an aerosolizer system with three or more aerosolizers each including a different substance. In one embodiment, the aerosolizer system is similar to the pod 150 illustrated in FIG. 3C which has three aerosolizers. Even though this disclosure generally refers to pods having three aerosolizers, or more than three aerosolizers, in other embodiments the pod has two aerosolizers in the cessation program operates to provide aerosol mixtures from the substances contained in the two aerosolizers, similar to what is described herein for a three aerosolizer embodiment.

At block 710, the process 700 controls the aerosol produced by each of the three or more aerosolizer's to form an aerosol mixture in an aerosol mixing chamber of the cessation system, the aerosol mixture formed based on a cessation program and can use information from one or more sensors to operate the cessation program. For example, one or more of the sensors illustrated in FIG. 4.

When the cessation device 100 operates to provide cessation program to a user, the controller circuit 130 executes cessation program instructions which causes signals to be provided to the aerosolizer drivers 110. The signals provided to the aerosolizer drivers 110 can be based on the cessation program instructions and on information that the controller circuit 130 receives from one or more of the sensors of the cessation device 100. For example, any one or more of (but not limited to) a flow sensor, an aerosol density sensor, and aerosol temperature sensor, an ambient temperature sensor, ambient pressure sensor, a blood oxygen sensor, and or the carbon dioxide sensor. The cessation program instructions may include instructions and information that was stored on the cessation device 100 when it was manufactured or configured, and/or instructions and information that were received by the cessation device 100 from the mobile platform 15, the server 25, and/or any other computer system.

In various embodiments, an aerosolizer system can include one, two, three or more than aerosolizers. In some embodiments, pods having a different number of aerosolizers may be used for different portions of the cessation program, and the (same) cessation device may be configured to work with pods having one, two, three or more aerosolizers.

In embodiments used with pods having a plurality of aerosolizers, the controller circuit 130 can provide, based on the cessation program, signals to the plurality of aerosolizer drivers 110 to cause the plurality of aerosolizers in the pod to produce an aerosol mixture having portions (e.g., percentages) of varying amounts of a plurality of substances in the pod. For example, for a pod having three aerosolizers in three substances in the pod (one corresponding to each aerosolizer), the cessation device can provide signals to the three aerosolizer drivers such that a first driver may drive a first aerosolizer to produce 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent (plus or minus 0.5%) of a "final" aerosolizer mixture. The cessation device (e.g., the controller circuit 130) can also provide signals to the three aerosolizer drivers such that a second driver may drive a second aerosolizer to produce 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent (plus or minus 0.5%) of the "final" aerosolizer mixture. The cessation device can provide signals to the three aerosolizer drivers such that a third driver may drive a third aerosolizer to produce 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 percent (plus or minus 0.5%) of the "final" aerosolizer mixture.

In addition, the cessation device (e.g., the controller circuit 130) can provide signals to the aerosolizer drivers 110 to produce aerosol from the different substances of different droplet sizes. For example, the controller circuit 130 can provide signals to three aerosolizer drivers such that the signals drive three corresponding aerosolizers in a pod to produce aerosol having the same droplet size, or two or more different droplet sizes.

In some embodiments, a cessation program is developed as part of the cessation system to wean an individual from smoking or vaping. Certain co-factors can be evaluated to create a cessation program or treatment plan for a unique user, as indicated in FIG. 7Q. FIGS. 7A, 7B-1, 7B-2, and 7C demonstrate how behavior modification and precision medicine may play into personalization domains that influence how a body processes nicotine. FIGS. 7D, 7E, 7F, 7G, 7H, and 7I illustrate the D-ADME$^2$ model that can determine how biological effects are elements of a smoking persona. FIG. 7J illustrates how psychosocial co-factors may result in a user being compelled to initiate a smoking experience. Finally, FIGS. 7K, 7L, 7M, 7N, 7O, and 7P demonstrate how persona and personalization parameters can be used to map cessation liquid variables.

In various embodiments, the cessation program can be created by a combination of biological, psychosocial, and clinical co-factors, otherwise known as a smoking persona. This information may be inputted as parameters that are used to control the cessation device to vary concentrations of the substances contained in the aerosolizer system at different points in a period of time during a cessation schedule for a certain person. Biological co-factors can be an individual's unique adaptation to nicotine related to their individual neurobiological phenotype. Psychosocial co-factors can be an individual's unique conditioned triggers to smoke with respect to personal and environmental conditions. Clinical co-factors can be severe psychological or cognitive challenges.

Additional parameter considerations may include smoking drivers and quit inhibitors. Managing smoking drivers and quit inhibitors to wean an individual off smoking or vaping can be a combination of cessation system use, behavioral software use, and medical consultation. The following table indicates possible smoking drivers or quit inhibitors, a description of each, and how the cessation system, software, or advisor/medical consultation may help.

| | Smoking Driver, Quit Inhibitor & Related Persona Element | Description/Example | Assessment | NoMore Device | Behavioral Software | Medical Consultation |
|---|---|---|---|---|---|---|
| Biological | Nicotine Dependence (Manage with Device) | Nicotine dependence varies across smokers. Some people have severe withdrawal, others have almost no withdrawal. Nicotine half-life is 2 hours so withdrawal may start 1 hour after smoking | Nicotine Metabolite Ratio (NMR) Fagerström FTND Question 1. Wisconsin Smoking Withdrawal Scale | Dependence level sets the Initial Nicotine Concentration Sets the Nicotine Taper Rate | | |

-continued

| | Smoking Driver, Quit Inhibitor & Related Persona Element | Description/Example | Assessment | NoMore Device | Behavioral Software | Medical Consultation |
|---|---|---|---|---|---|---|
| | Sensory Experience (Manage with Device) | Some people enjoy the sensations of smoking while others do not. People like different amounts of "throat hit" People like different flavors | 1. How much do you enjoy smoking? 2. How much to like the feeling of inhaling cigarette smoke? 3. How much do you like the feeling of "nicotine burn"? 4. What flavor do you like? | Use desired throat hit to set $\alpha fb$ to an initial setting. Then reset $\alpha fb$ during nicotine taper when nicotine concentration is low. | | |
| Psychosocial | Triggers (Manage with Behavioral Tech) | i. External stimuli (the smell of smoke, movie) ii. Daily routine (e.g., after each meal, driving, phone) iii. Places (their chair, outside) iv. Emotions (celebration, anger, loneliness, boredom) v. Social situations vi Stressful events vii. Alcohol/other substances | Ask about each category of trigger + give example. Ask how much does this trigger drive your smoking. | | Before the quit smoking day, develop a strategy for managing each category of trigger. This will include the use of NoMore, and will include other strategies as well. | |
| | Social Smoking (Manage with Behavioral Tech) | Social smoking can be difficult to overcome because it involves group identification, social acceptance. This is a bigger problem for younger people. | Do you sometimes smoke with others? If yes, Who do you smoke with? | | Add "Social Module" to plan - 1. Tell friend you will use NoMore. 2. Ask friend not to smoke. 3. Stop seeing friend. | |
| | Ritual Smoking (Manage with Device and Behavioral Technology) | Older smokers in particular, tend to show increased ritual smoking - smoke the same number of cigs each day with their daily routine | Ask about daily routine (Part of triggers survey) | Extend taper to 12 weeks, will likely need a long period after taper also. | Introduce plan to replace routine cigarettes with NoMore (e.g., use NoMore after each meal) | |
| | Stressful Event (Manage with Device and Behavioral Technology) | Stressful event may be very small to very large. A stressful event is the number 1 reason for relapse back to smoking. Relapse occurs because of high stress in combination with poor coping skills. | 1. Did you ever quit smoking before? 2. If yes, what led to relapse? 3. What portion of your cigarettes do you smoke due to stress? 4. How much has stress kept you from quitting? | Use of Rescue Dose The dosing will be set up | Mindful use of NoMore, Mindfulness of emotions. Pause, recognize the stressful situation, recognize your response to the situation. Decide what to do. | |
| | Attachment (Manage with Behavioral Tech) | Some feel cigarettes are their "best friend." They can cut down to 1 cig/day, but cannot stop. Grieving occurs after stopping | "Have you ever thought of smoking as a close friend?" Also -Device check: if they are unable to quit smoking after tapering down cigs or unable to stop product after tapering down | | Training in letting go, grief counseling | Inability to quit may require medical consult if person is stuck. |

-continued

| | Smoking Driver, Quit Inhibitor & Related Persona Element | Description/Example | Assessment | NoMore Device | Behavioral Software | Medical Consultation |
|---|---|---|---|---|---|---|
| Clinical | Alcohol/Substances (Manage with Behavioral Tech and possibly with Medical Consult) | Alcohol/substance use is common in smokers and highly associated with relapse. 1. Alcohol and smoking can be associated as a routine, 2. Increases smoking urges. 3. Alcohol decreases ability to exert will power and increases automatic smoking. | 1. On average, how many days per week do you drink? 2. What is the most number of drinks you will have in a day? | | 1. While drinking, can a person use NoMore instead of smoking? If yes, continue drinking as before 2. If no, then reduce drinking to 1 drink per day. | 3. If they continue to smoke while drinking, and are unable to cut down, this requires a Medical Consult |
| | Depression (Manage with Behavioral Tech and possibly with Medical Consult) | Severe depression is highly associated with inability to quit and relapse | PHQ-2 > 3 do PHQ-9 PHQ > 4 - see B Technology PHQ-9 > 9 Get consult | | PHQ > 4 add depression component to behavioral approach | PHQ > 9 requires medical consult |
| | Anxiety (Manage with Behavioral Tech and possibly with Medical Consult) | Severe anxiety is highly associated with inability to quit and relapse | GAD-2 > 3 do GAD-7 GAD > 4 - see Beh. Technology GAD-9 > 9 Get consult | | GAD > 4 - add anxiety module to behavioral approach. | GAD-9 > 9 requires medical consult |
| | Low Change Capacity (Manage with Medical Consult) | People with traumatic brain injury, cognitive impairment, dementia, late stage schizophrenia may smoke as a ritualized behavior, may smoke more e.g., 3-4 packs per day. | Ask - do you have a history of traumatic brain injury, cognitive impairment, dementia, late stage schizophrenia, or similar? | | | Requires a medical consult |

Figure 7C:
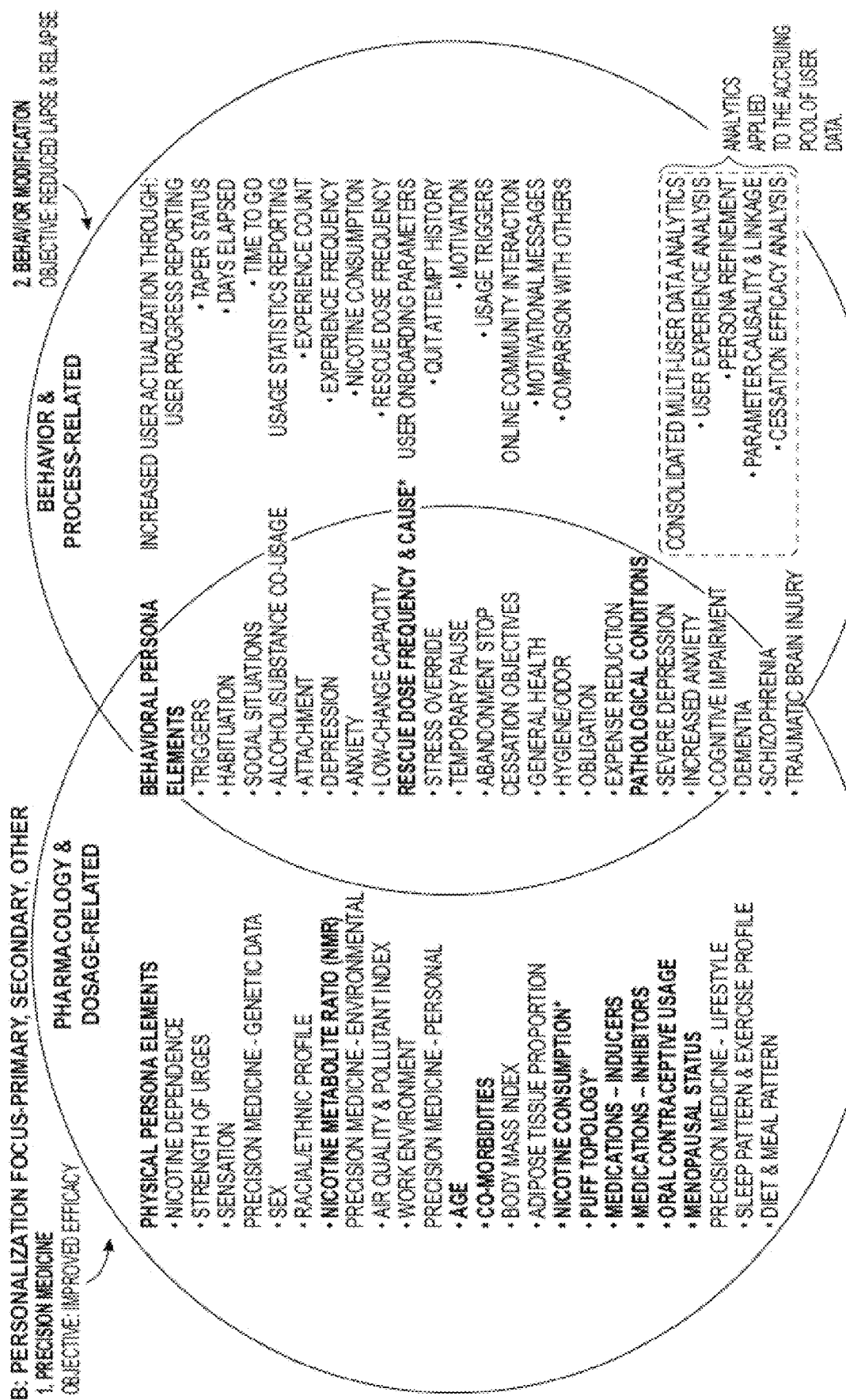
FIG. 7C is a diagram illustrating an example of primary, secondary, and other focused personalization domains utilized by the smoking cessation system.
Figure 7D:
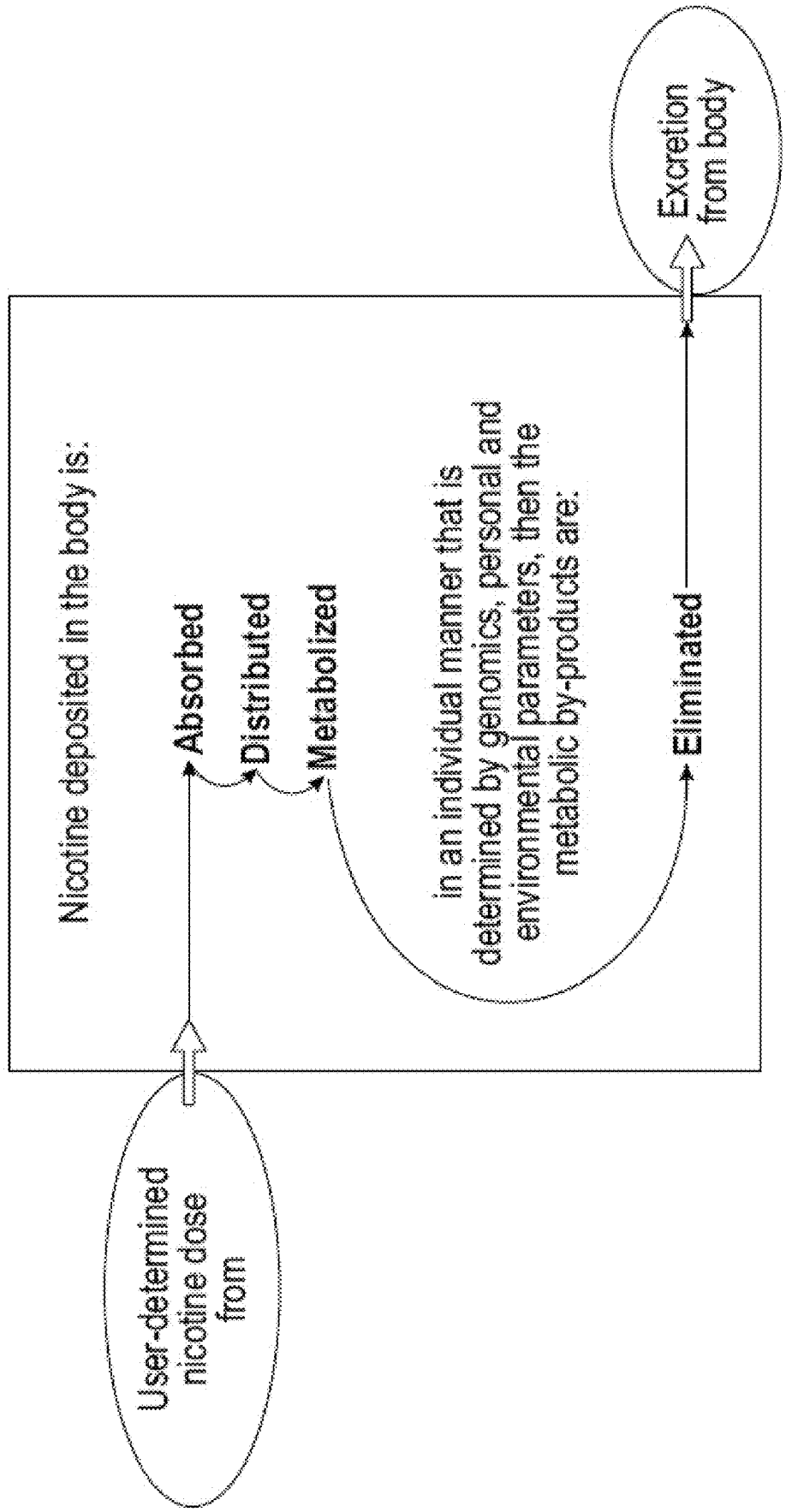
FIG. 7D is a diagram illustrating an example of how nicotine is deposited within the body, according to one embodiment.
Figure 7E:
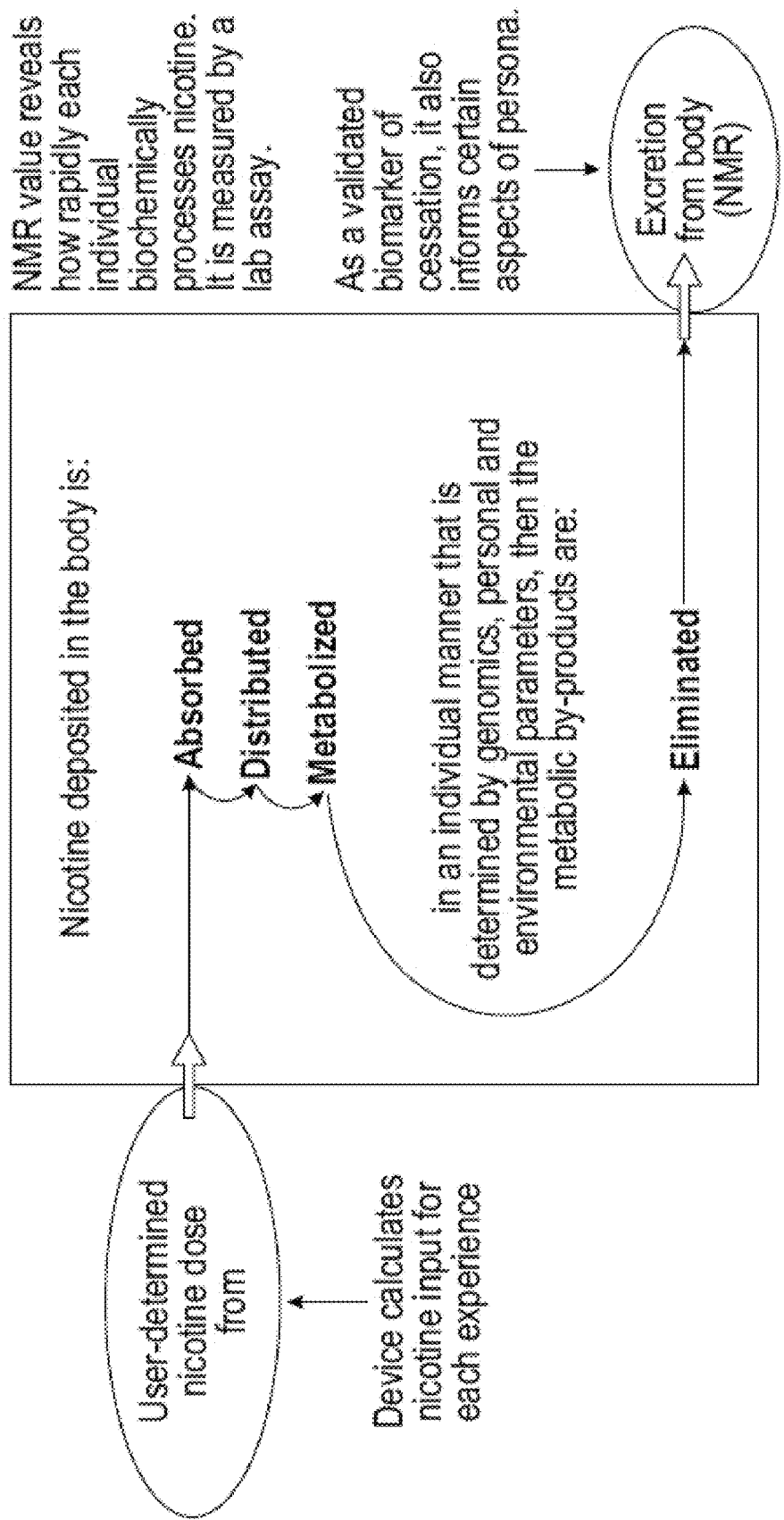
FIG. 7E is a diagram illustrating an example of how nicotine input and output are measured, according to one embodiment.
Figure 7F:
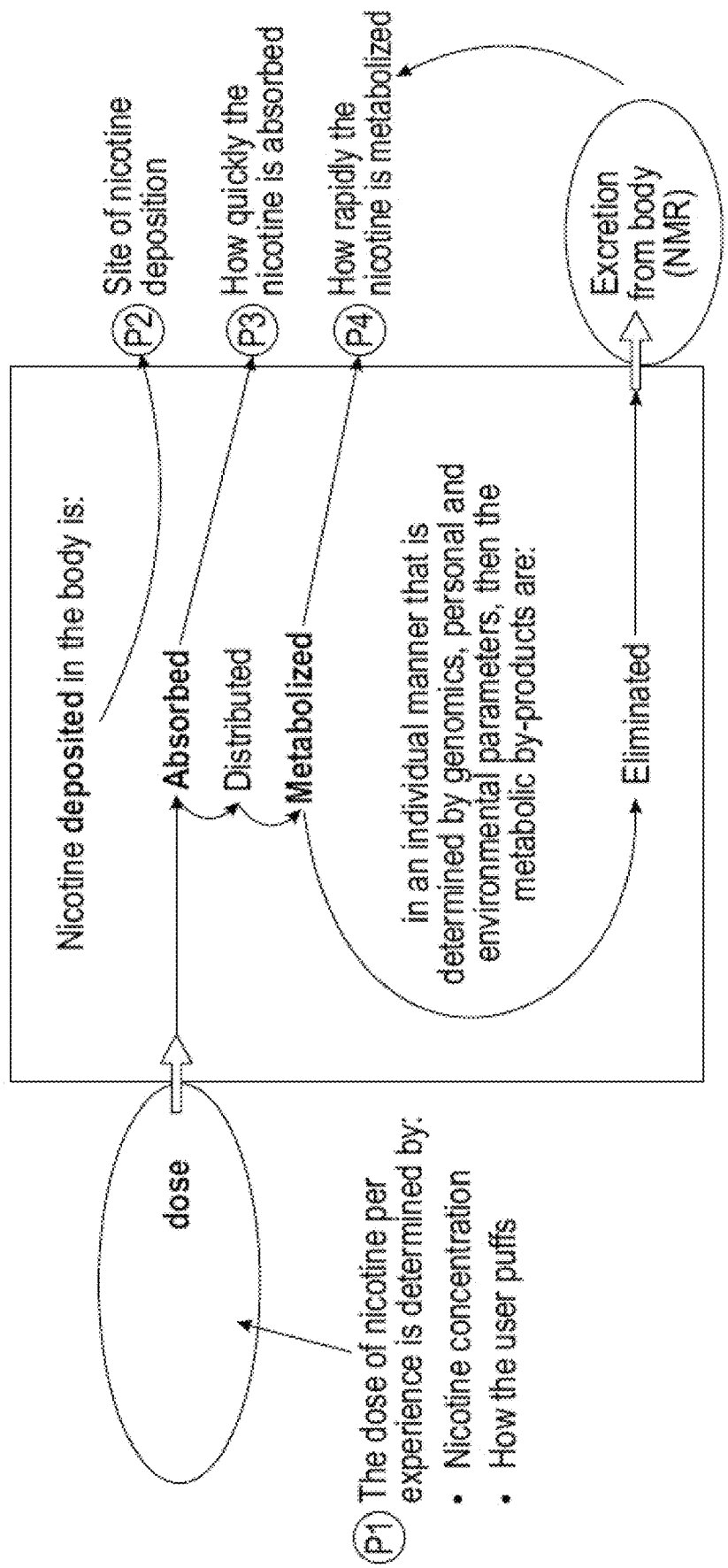
FIG. 7F is a diagram illustrating an example of four key personalization parameters and their effect on nicotine deposited in the body.
Figure 7H:
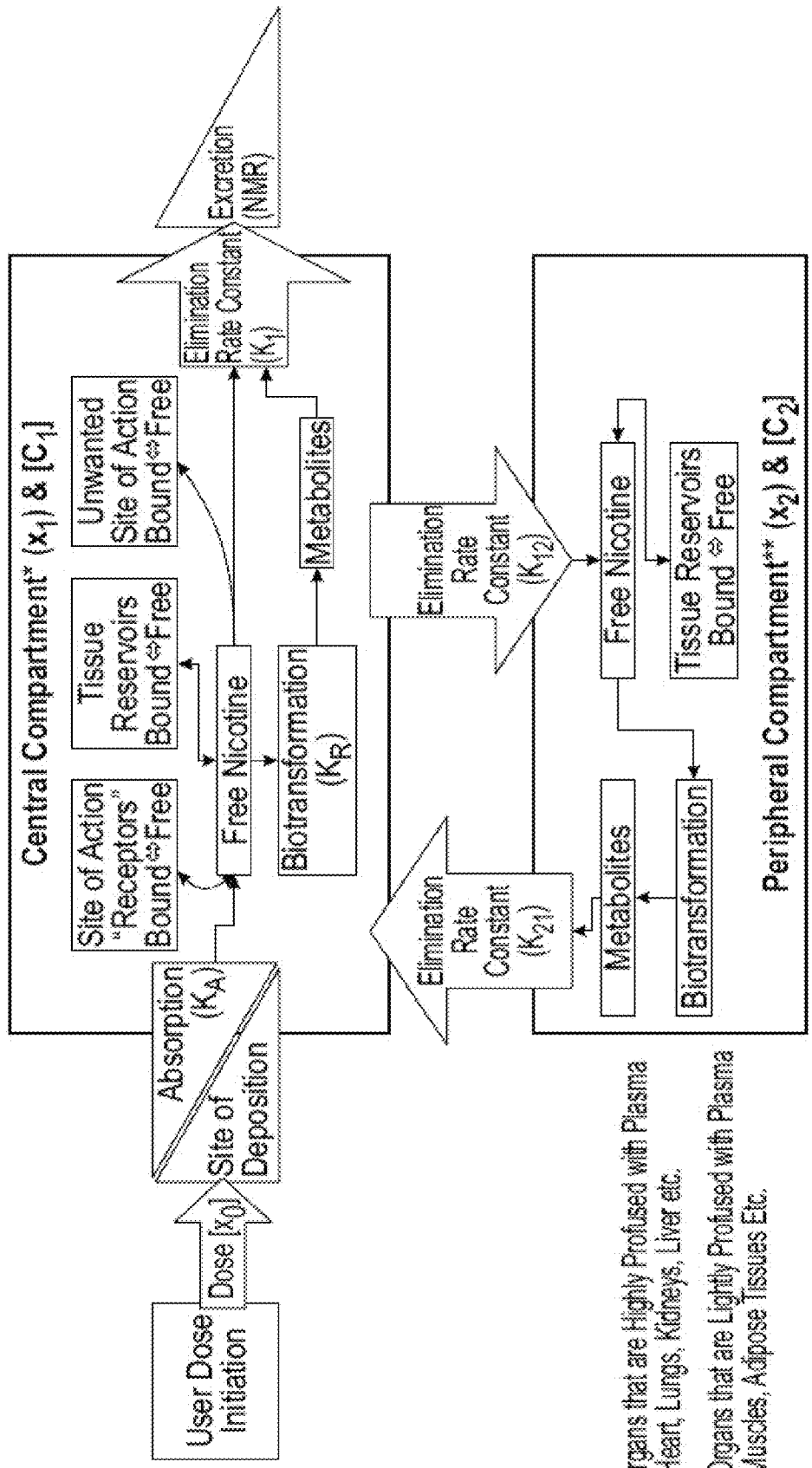
FIG. 7H is a diagram illustrating the cascaded D-2ADME personalization model.
Figure 7I:
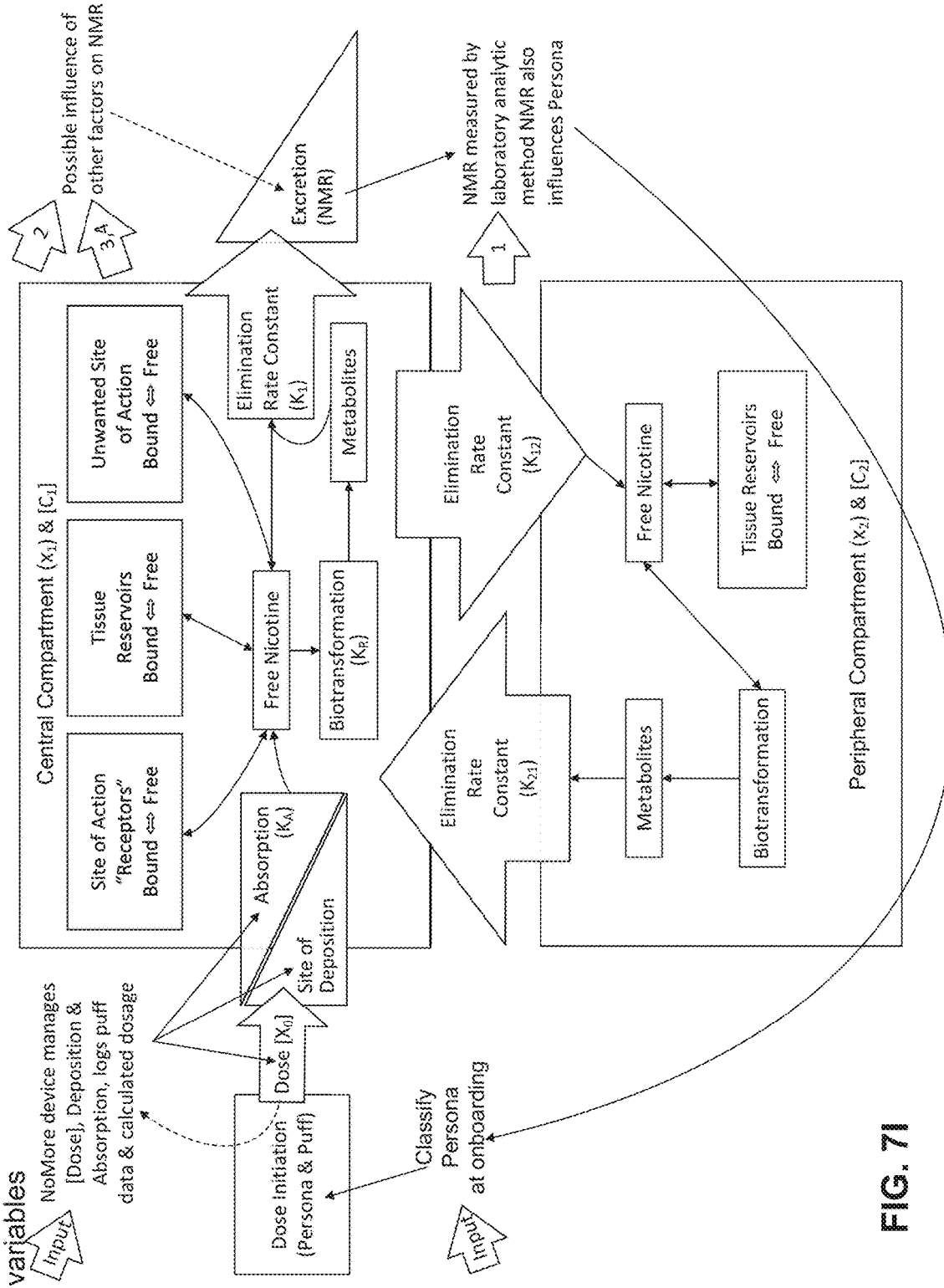
FIG. 7I is a diagram illustrating the personalized parameters and device managed variables used in the smoking cessation system.
Figure 7J:
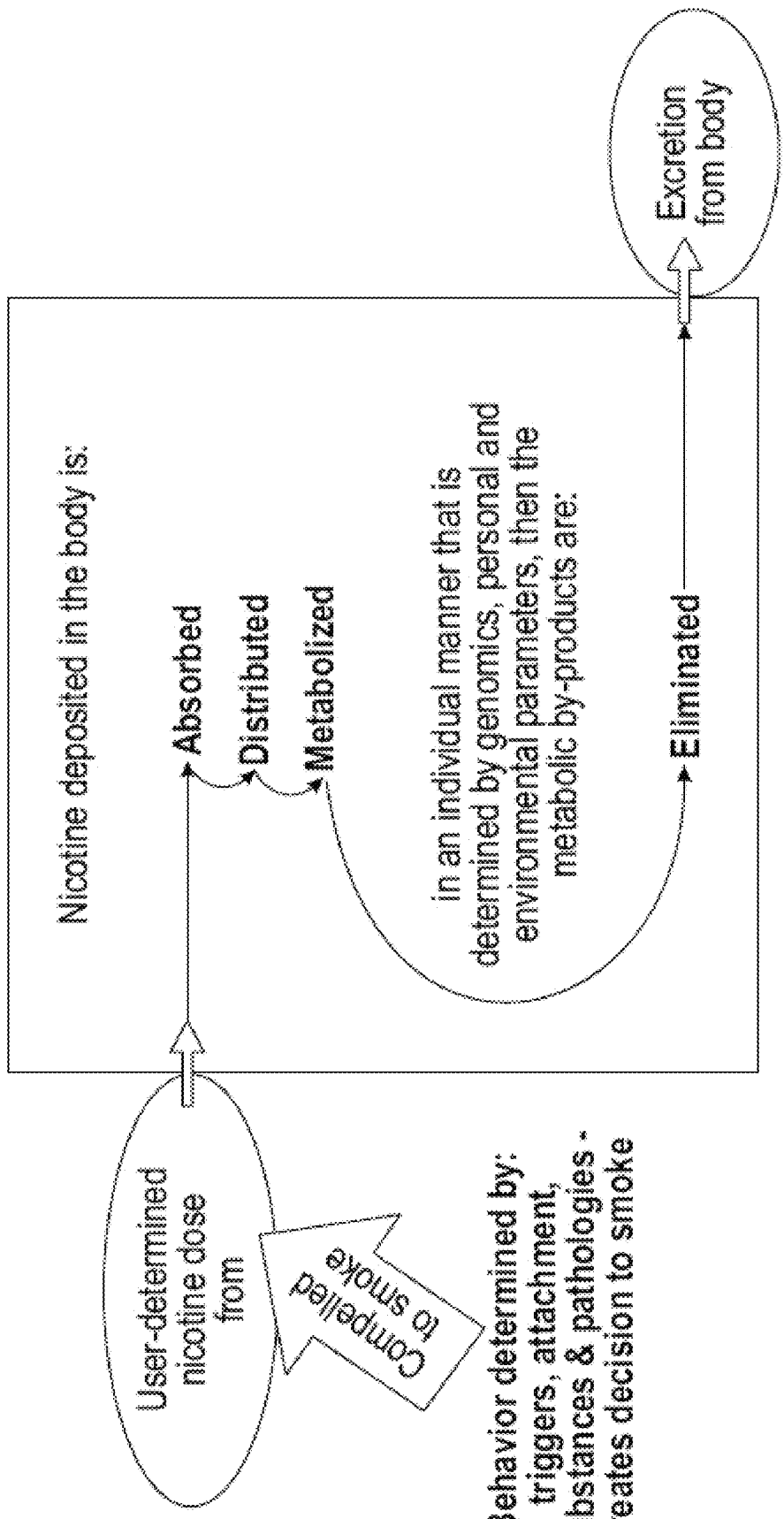
FIG. 7J is a diagram illustrating the psychosocial co-factors when a user is being compelled to initiate a smoking experience.
Figure 7K:
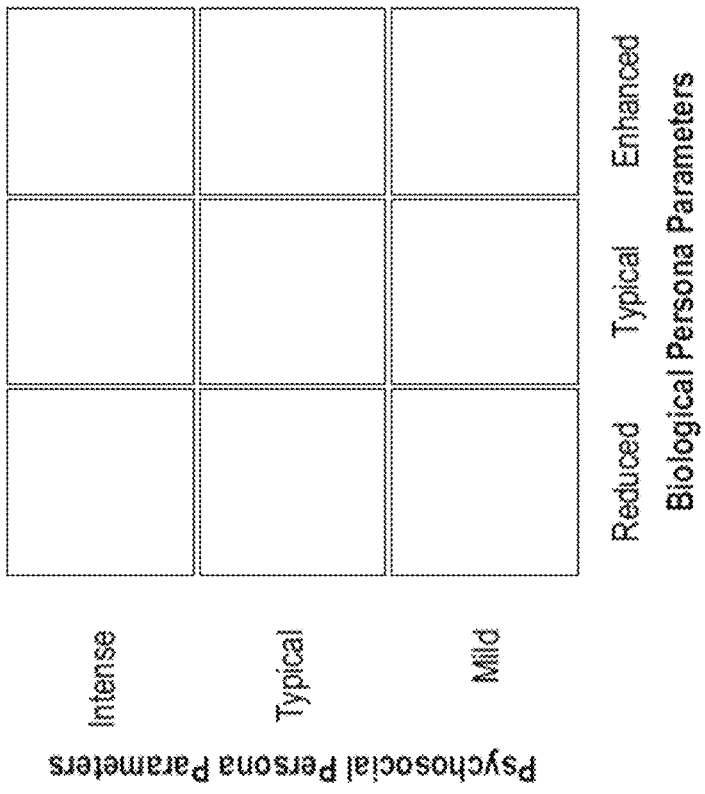
FIG. 7K is a diagram illustrating how personalization parameters and clustered persona characteristics are used to map cessation liquid parameters.
Figure 7M:
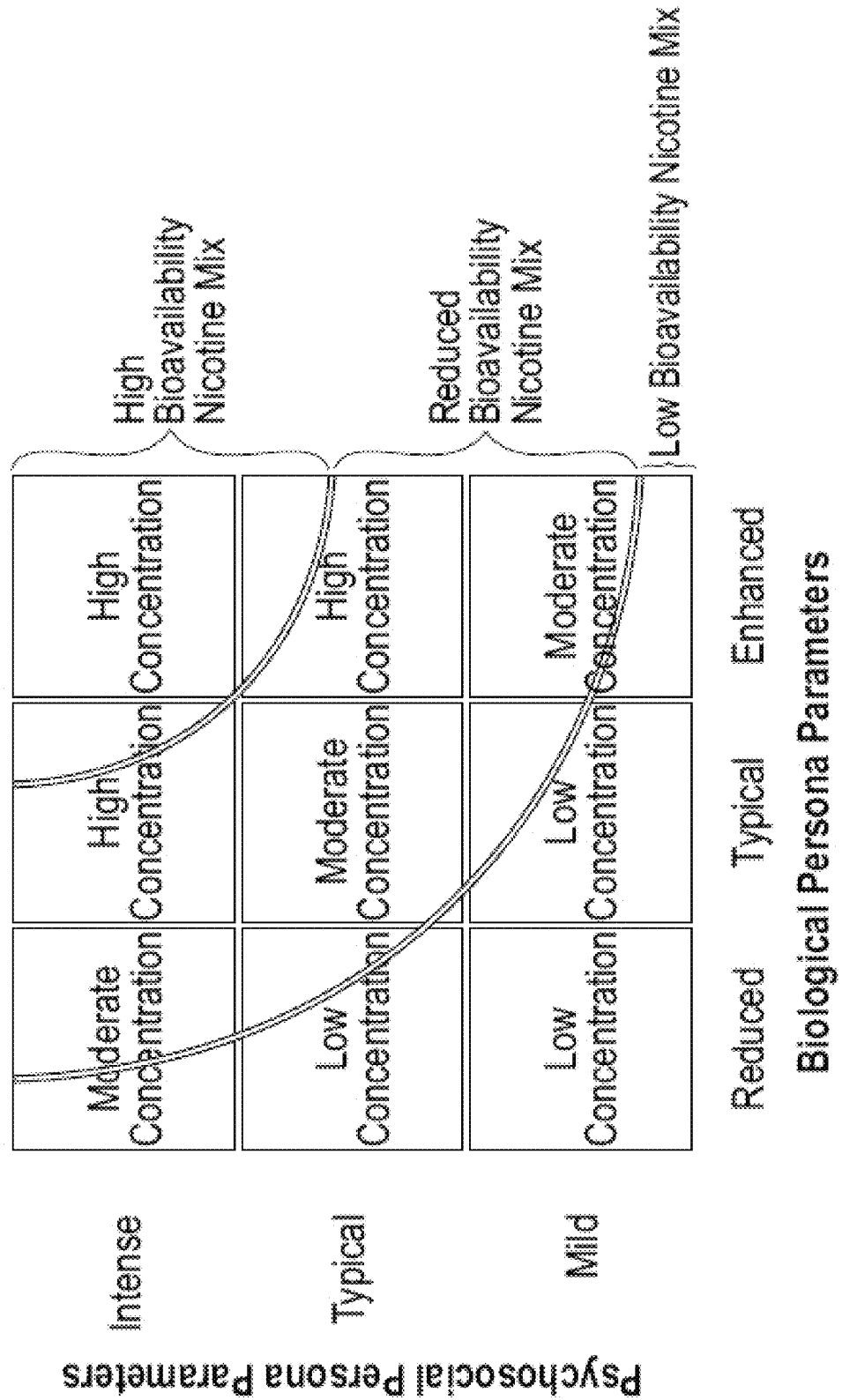
FIG. 7M is a diagram illustrating bioavailability mapped to persona and metabolism rate.
Figure 70:
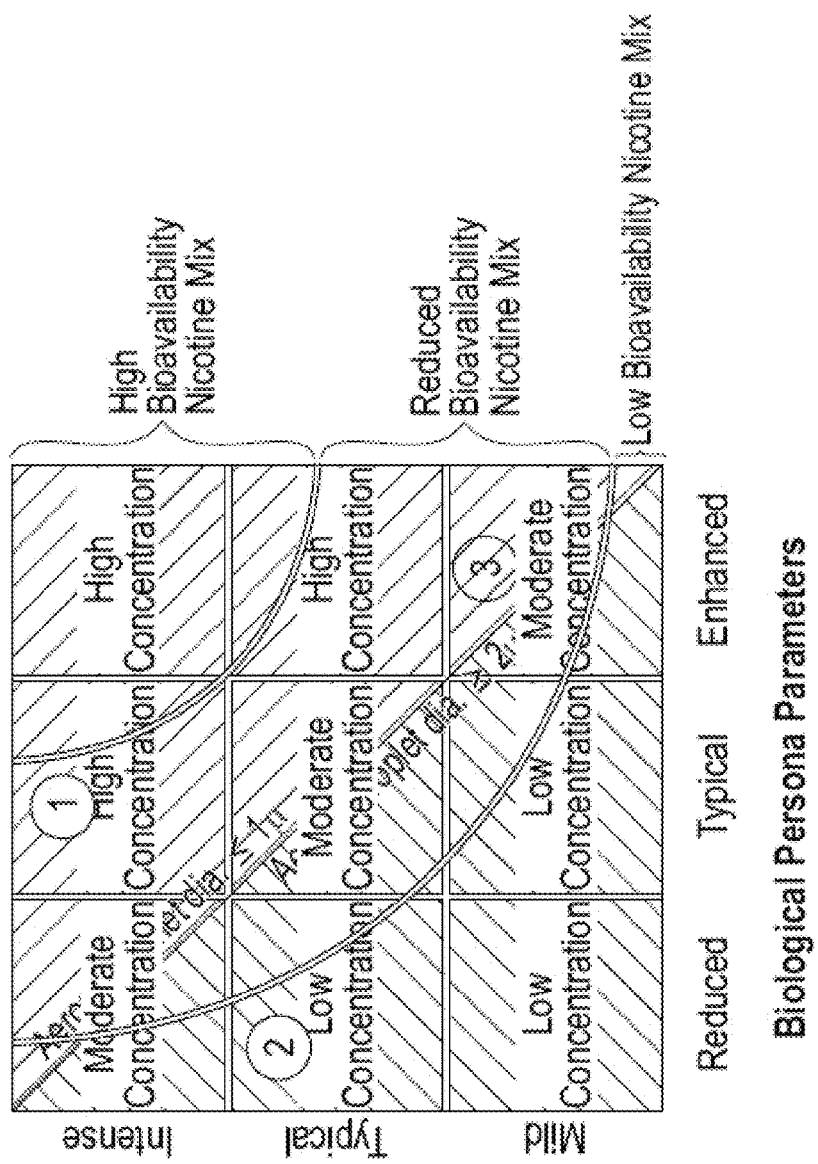
Figure 7Q:
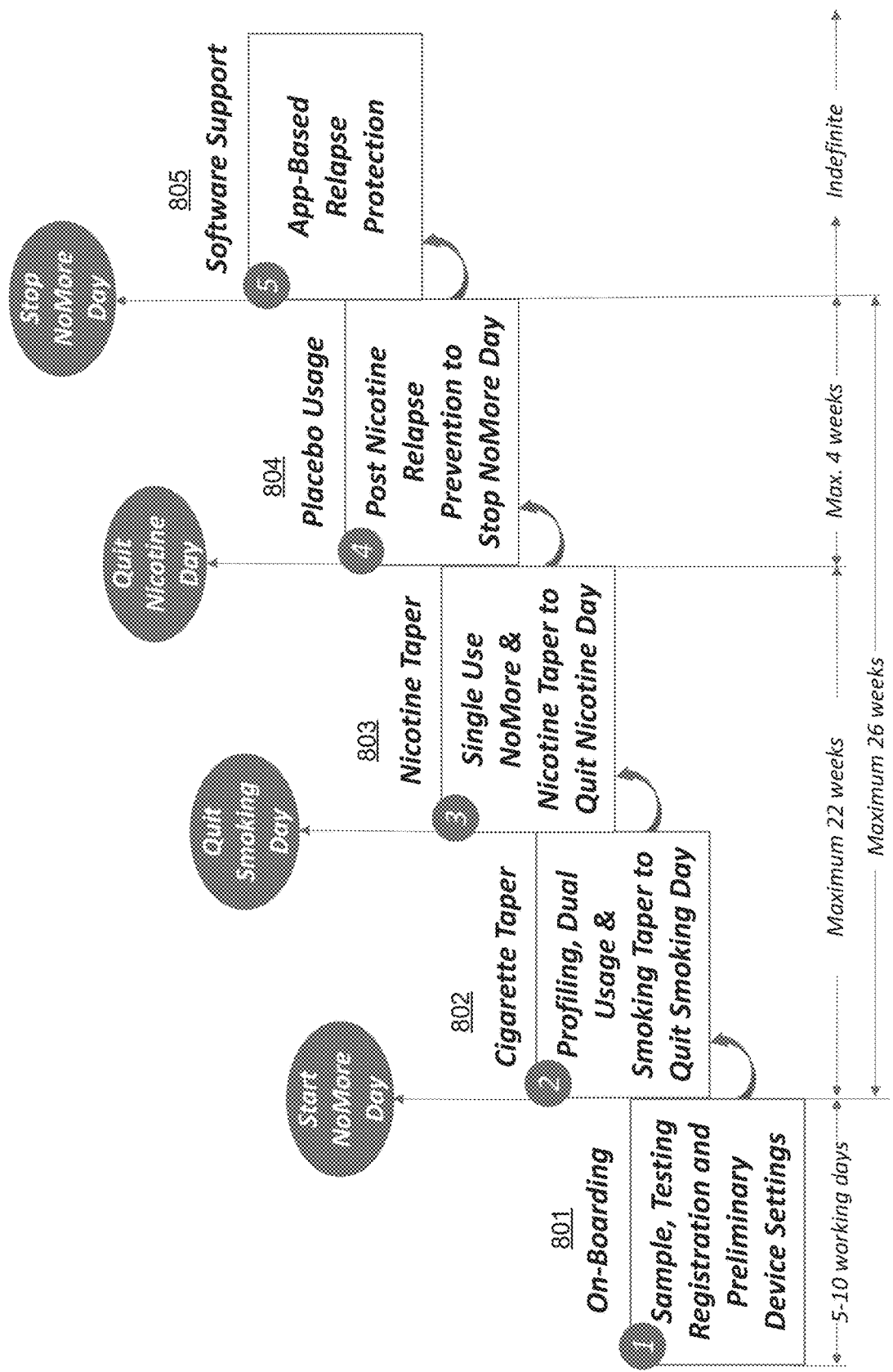
FIG. 7Q is a diagram illustrating a five step process that can be implemented for a cessation program.

FIG. 7Q is a diagram illustrating a five-step process that can be implemented for a cessation program including on-boarding 801, cigarette taper 802, nicotine taper 803, placebo usage 804, and software support 805 phases.

In examining the five phases in more detail, the objectives of the on-boarding phase 801 may be to register and enroll a user and to do preliminary device configuration. This on-boarding phase 801 may begin with an appointment with a prescribing physician and end with NMR analytical results. Some steps for dosage calculation may include obtaining a saliva sample for analytical NMR determination, identifying a likely consumable category based on persona, creating a preliminary definition of cessation liquid initial values based on persona, confirmation of age, a physician interview to assess menopausal status, co-morbidities, medications, lifestyle factors, creating a preliminary definition of taper path and taper rate based on age and persona, and configuring NMR input upon receipt of laboratory results.

Some psychosocial and clinical actions included in the on-boarding phase 801 may include defining an aspirational definition of cessation process duration, qualitative determination of three persona elements S—S—S, an overview of the behavioral program in subsequent steps (education, identification of triggers, managing urges, managing stress, the smoking taper, the quit process), overview of social support, overview of professional support, physician interview to identify presence of/susceptibility to additional behavioral components (uncontrolled severe stress, generalized anxiety disorder, depression, bipolar disorder, post traumatic stress disorder, pre-existing traumatic brain injury, schizophrenia), and to set a date for profiling.

Other actions included in the on-boarding phase 801 can include various registration activities, subscription to consumables delivery service, user specification of flavor system (tobacco, menthol none), or enlist willing onboarded cessation system users under the auspices of a "pay it forward" strategy to help two other people quit once they have successfully quit.

In some embodiments, the second phase of the cessation program may be a cigarette taper phase 802 which may include profiling and product familiarization. Objectives of this cigarette taper phase 802 may be to finalize personalization, define start delivery parameters, or set a quit smoking day. This phase may start immediately after NMR results are configured and end with a successful quit smoking day.

Some steps for dosage calculation may include setting initial delivery parameters to match cigarette experience based on persona data. In one example, set initial nicotine concentration r=3% w/w, initial free fraction $\alpha fb$=0.03, for light smoker <1 pack/day with low NMR. In another example, set initial nicotine concentration r=5% w/w, initial free fraction $\alpha fb$=0.07, for heavy smoker >1 pack/day with elevated NMR. In yet another example, set initial aerosol droplet size $\delta \leq 1.0$ µm.

Another dosage calculation action may be setting initial PRN/rescue concentration higher than standard but with same $\alpha fb$ and $\delta$ according to persona. For example a light smoker r=5% w/w and a heavy smoker r=7% w/w.

Other dosage calculation actions may include 5 day and 10 day parameter ranging evaluation (including systemic increasing and decreasing around initial settings and PRN dose settings for r and $\alpha fb$ with $\delta$ constant to establish final parameter values for the objective of a satisfying and pleasant routine dose or maximally satisfying and tolerable PRN dose), recording of user puff topology to enable dose calculation, finalize delivery parameters and update program configuration, or confirmation or adjustment of cessation taper duration for subsequent step.

Psychosocial and clinical actions in the cigarette taper phase 802 can include to define a Quit Smoking Date (QSD) (estimate 2-4 weeks from beginning of Dual Usage phase) comprising: cessation program learning/adaptation period (5-10 days) using initial delivery parameter values from the on-boarding phase 801, or dual usage (14-21 days) with cigarette taper (steps below).

The cigarette taper:
- Techniques for smoking tapering: 1) ad-lib; 2) frequency reduction (only every hr ~16/day, then only every 2 hrs~8/day); 3) scheduled smoking (on waking, after eating, and one in the evening ~5/day).
- Using selected technique to cut cigarette smoking in half to 10/day in the first 50% of time to QSD; then again in half to 5/day at 75% to QSD; then zero when QSD has been reached.
- Replace cigarette reduction with NoMore usage.

Another psychosocial action may be progressive behavioral training (education concerning health risks like lung cancer, COPD, and heart disease, identification and recording of triggers like temporal, association, emotional, location, and alcohol, or mindfulness training for stress management), a call with a professional counsellor 2-3 days before Quit Smoking Day to enhance chance of behavior change, or calls with former cessation program users as quit advisors.

Other actions in the cigarette taper phase 802 may include a cessation program training video to cover inhalation changes with respect to reduced rate & increased depth, how the cessation program is different from smoking, function of lights and buttons, battery recharging, replacing consumables, or general usage recommendations for learning period. Other actions may also be configuration of consumable replenishment schedule. One action may cover steps to take if Quit Attempt is unsuccessful: do not progress to the nicotine taper phase 803, re-evaluate and assess what went wrong, create a new strategy based on what went wrong (if stress, then stress management behavioral therapy, if motivation/social, then enhance social support elements, or if technical, then review product information/video), engage medical support if simply not engaged, set new Quit Day in 2-4 weeks & make plan to prepare for it, or reset taper and start cigarette taper phase 802 again.

In some embodiments, the third phase of the cessation program may be a nicotine taper phase 803 which may include the objective to end the use of nicotine. This phase may start after a successful quit smoking day and end when cessation taper reaches final dose of nicotine level.

In some embodiments, the steps for dosage calculation may include not changing the previously established PRN/rescue settings, beginning cessation taper from previously defined start conditions for nicotine concentration, free fraction, and aerosol droplet size, starting taper two weeks after beginning the nicotine taper phase 803, applying taper variables and rate according to the previously defined taper parameters, monitoring PRN/rescue usage and adjusting taper variables if it is determined that the taper is too fast, or not long enough in duration.

Regular high PRN use >10× on consecutive days (3-4):
- Indicates standard dose insufficient. Re-evaluate taper and consider adjustment.
- Consult with user concerning dosage increase.
- Re-test to determine threshold for routine dose; reset taper to this new dosage; reduce taper rate.

At final dose likely nicotine concentration p<1% w/w:
- Increase aerosol $\delta \geq 2.0$ μm to reduce absorption rate & peak
- Increase free ratio $0.01 \leq \alpha_{fb} \leq 0.03$ to give throat hit.

In some embodiments, the psychosocial actions may include defining a date for taper to reach final dose nicotine and the end of the nicotine taper phase 803 (clearly defined date with total use of cessation program not to exceed 26 weeks). Other psychosocial actions may include recording clearly defined date and time, or monitoring PRN/rescue dose usage, assisting with recognition of stressful events & management without smoking.

If Lapse occurs (use of 1-2 cigs/day plus cessation program):
- Counselling, evaluation, encouragement to restart.
- Consider taper adjustments.

If Relapse occurs (return to full smoking at level present starting the cigarette taper phase 802):
- Restart at beginning of the cigarette taper phase 802.
- Consider taper adjustments.

If repeated taper reset, relapsing and failure in the nicotine taper phase 803:
- Ensure cessation program is not regarded as a recreational product that can be used forever.
- Allow for 2-3 potential taper resets in high-dependence users.
- Allow for possible extension of total Quit Process time on condition of medical consult.

In taper "tail" phase with final dose extremely low, expect phase to last 2-6 weeks:
- NoMore as crutch in this phase.
- PRN/rescue doses still available.

At final dose, assess user and consider prolonged usage as long as total usage does not exceed 26 weeks.

Other actions in the nicotine taper phase may include preparing for transition out of cessation program use or preparing for provision of potential support for others in the online community.

In some embodiments, the fourth phase of the cessation program may be a placebo usage phase 804 which may include the objectives of no nicotine consumption and no user relapse. This phase may start after successful Quit Day or 26 weeks, whichever first. The phase may end with no grieving or withdrawal symptoms. The psychosocial & clinical actions may include defining post-quit duration, monitoring to ensure no physical withdrawal symptoms, support for potential grief management, ongoing behavioral modification support (proactive recognition of stressful events or stress management without resorting to smoking), or recording of triggers and cues (uploading for monitoring and behavioral support).

Other actions in the placebo usage phase 804 may include video training for potential role as coach and support resource in online cessation program community.

In some embodiments, the fifth phase of the cessation program may be a software support phase 805 which may include the objective of stopping the use of the cessation program. The phase may end when the user decides. Dosage actions in this phase may include cessation system device usage disabled unless intended use is transitioned from Cessation to Reduced Exposure & Reduced Risk. One psychosocial action may include community reinforcement support. Other actions may include active participation in Online Support "pay it forward" community or potential intended use transition to Reduced Exposure & Reduced Risk in certain extreme cases.

FIG. 7A is a diagram illustrating pharmacological dosage related personalization data and behavior modification as two intersecting domains of cessation program personalization.

FIGS. 7B-1 and 7B-2 are a two-part table illustrating personalization parameters that influence how the body processes nicotine and how each may be quantified. The personalization parameters can be divided into primary, secondary, and tertiary/quaternary parameters based on prioritization.

FIG. 7C is a diagram illustrating an example of primary, secondary, and other focused personalization domains utilized by the smoking cessation system which were previously illustrated in FIG. 7A and FIGS. 7B-1 and 7B-2.

FIG. 7D is a diagram illustrating the basic model components of D-ADME[2] and how nicotine may be deposited within the body. As the figure indicates, nicotine can be absorbed, distributed, and metabolized based on an individual's genomics and personal and environmental factors. The byproducts from this process can be eliminated and excreted from the body. FIG. 7D demonstrates how biological co-factors can help define a smoking persona.

FIG. 7E is an example of how calculating nicotine input and measuring nicotine output can determine how an individual metabolizes it, often called the Nicotine Metabolite Ratio (NMR). In some embodiments, NMR may be calculated for an individual to reveal how rapidly an individual biochemically processes nicotine. This information can be applied to form an individual's persona and be input parameters for a cessation program.

FIG. 7F illustrates the same diagram as FIG. 7D and how nicotine is deposited in the body. Additionally, the diagram identifies four key personalization parameters that can be configured for use in a cessation program. In some embodiments, four parameters include the dose of nicotine received by the user when using a cessation device, the site of the nicotine deposition, how quickly the nicotine is absorbed, and how rapidly the nicotine is metabolized.

FIG. 7G contains the four key personalization parameters as illustrated in FIG. 7F, but in this embodiment, shows three critical variables of the cessation liquid and aerosol that can affect the personalization parameters. In some embodiments, three critical variables include nicotine concentration, aerosol droplet size, and free nicotine ratio.

FIG. 7H is an example embodiment of the detailed cascaded D-2ADME personalization model illustrating the central compartment and the peripheral compartment.

FIG. 7I takes the same cascaded personalization model of FIG. 7H and illustrates how adding personalized user persona information and configuration of the cessation device can affect NMR.

FIG. 7J is a diagram illustrating how psychosocial co-factors can affect how nicotine is deposited in the body when a user is compelled to smoke. Psychosocial co-factors, as discussed previously, can include triggers, attachment, substances, and pathologies.

FIG. 7K is a diagram illustrating how personalization parameters and clustered persona characteristics can be used to map the magnitude and range of associated cessation liquid parameters. The intersection of biological persona parameters and psychosocial persona parameters can create varying levels of cessation liquid necessary for a cessation program.

FIG. 7L illustrates the diagram of FIG. 7K with low, moderate, or high nicotine levels according to persona level. In one embodiment, reduced biological persona parameters with mild psychosocial persona parameters would result in a low concentration of concentrated nicotine for a cessation program. In an alternate embodiment, enhanced biological persona parameters paired with intense psychosocial persona parameters may result in a recommended high concentration of nicotine.

FIG. 7M adds to the FIG. 7L to illustrate bioavailability of nicotine across personas.

FIG. 7N adds to FIG. 7M to illustrate how aerosol droplet size is mapped to persona profile and metabolism rate. In one embodiment, a larger aerosol droplet may result in a higher concentration at a pulmonary deposition. In another embodiment, a smaller aerosol droplet may result in a lower concentration at a buccal deposition.

FIG. 7O adds to FIG. 7N illustrating how frequency of smoking and puff topology can add to the uniqueness of the cessation liquid variables for a user. In one embodiment, a middle-aged, heavy smoker, typical metabolizer, severe withdrawal symptoms, elevated smoking urges, enhanced sensory enjoyment, intense alcohol use, and elevated smoking attachment may result in a higher concentration of nicotine for the user.

FIG. 7P illustrates how the users from FIG. 7O can benefit from a unique cessation program based on cessation start point, age, behavioral information related to triggers, stresses, anxiety, depression, alcohol consumption, and social cue responses. In one embodiment, the cessation program may create unique taper paths, taper rates, and program durations for different users.

System Implementation

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

A non-transitory computer readable storage medium can be a tangible device that can retain and store data and/or instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Java, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a standalone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A smoking cessation system, comprising:
    a cessation device including
        a housing having a distal end and a proximal end;
        a channel in the housing, the channel having an opening on a distal end of the channel for receiving air and an opening positioned on a proximal end of the channel to communicate air to an aerosolizer pod coupled to the housing;
        an aperture on the proximal end of the housing configured to receive the aerosolizer pod therein, the housing configured to at least partially surround the aerosolizer pod when the aerosolizer pod in positioned in the housing;
        a flow sensor positioned to sense air flowing through the channel;
        a first aerosolizer driver, a second aerosolizer driver, and a third aerosolizer driver configured to electrically couple to a first aerosolizer, a second aerosolizer, and a third aerosolizer, respectively, of the aerosolizer pod;

a rescue button;

a power source; and a controller circuit coupled to the power source, the controller circuit comprising a hardware controller coupled to the flow sensor, the first, second, and third aerosolizer drivers, and the rescue button, the hardware controller including a hardware processor and a non-transitory computer readable medium in communication with the hardware controller, the computer readable medium configured to store smoking cessation program information, and to store executable instructions that, when executed, configure the hardware controller to perform a smoking cessation program that includes receiving input signals from the flow sensor and the rescue button, and individually controlling the first, second and, third aerosolizer drivers to provide aerosolizer generation signals to control the first, second, and third aerosolizers of the aerosolizer pod to generate an aerosol mixture based at least on the received input signals and the smoking cessation program information.

2. The cessation system of claim 1, further comprising the aerosolizer pod, and wherein the aerosolizer pod comprises an intake port for receiving air from the channel;

an exhaust port for communicating the aerosol mixture out of the aerosolizer pod;

an aerosolizer system comprising the first, second, and third aerosolizers, the first, second, and third aerosolizers each including an electrical connection that electrically couples to the first, second, and third aerosolizer drivers, respectively, when the aerosolizer pod is received into the housing.

3. The smoking cessation program of claim 2, wherein the aerosolizer pod further comprises an ID chip, and wherein the cessation device further comprises an aerosolizer pod interface configured to sense the ID chip and communicate the ID chip to the hardware controller.

4. The cessation system of claim 2, wherein the aerosolizer pod further comprises an aerosol mixing chamber having walls that define a mixing space, the mixing chamber having intake openings in fluid communication with the first, second, and third aerosolizers and an exhaust opening in fluid communication with the pod exhaust port such that aerosol generated by the first, second, and third aerosolizers can enter the mixing chamber via the intake openings, mix together, and be communicated to a user via the pod exhaust port.

5. The cessation system of claim 4, wherein the first aerosolizer includes a first container for holding a first substance;

the second aerosolizer includes a second container for holding a second substance; and the third aerosolizer includes a third container for holding a third substance.

6. The cessation system of claim 5, wherein each of the first, second, and third substances is a different substance.

7. The cessation system of claim 5, wherein the first substance comprises nicotine.

8. The cessation system of claim 1, wherein the controller circuit further comprises a transceiver, and an antenna coupled to the transceiver, the transceiver configured to receive smoking cessation program information from a mobile platform via the antenna.

9. The cessation system of claim 8, further comprising the mobile platform, the mobile platform configured to communicate with the cessation device to receive operational use information from the cessation device and provide updated smoking cessation program information to the cessation device.

10. The cessation system of claim 9, wherein the operational use information is based at least in part on one or more of signals received by the hardware controller from the flow sensor.

11. The cessation system of claim 10, wherein the operational use information is additionally based at least in part on one or more of signals received by the hardware controller from the rescue button.

12. The cessation system of claim 10, wherein the cessation device further includes a first temperature sensor, a second temperature sensor, and a third temperature sensor each configured to sense a temperature of aerosol generated by the first, second, and third aerosolizers, respectively, and to communicate a corresponding signal, and wherein the operational use information is additionally based at least in part on one or more of signals received by the hardware controller from the first, second, and third temperature sensors.

13. The smoking cessation system of claim 9, further comprising a cloud-based back-end computing system configured to receive operational use information from the mobile platform and provide the updated smoking cessation program information to the mobile platform.

14. The cessation system of claim 8, wherein the cessation device is configured to communicate operational use information via the transceiver, wherein the operational use information is based at least in part on one or more of signals received by the hardware controller from the flow sensor.

15. The cessation system of claim 8, wherein the cessation device is configured to communicate operational use information via the transceiver, wherein the operational use information is based at least in part on one or more of signals received by the hardware controller from the rescue button.

16. The cessation system of claim 1, further comprising a fingerprint sensor coupled to the hardware controller, wherein the executable instructions further configure the hardware controller receive an input from the fingerprint sensor and activate the cessation device for use only when the fingerprint matches an authorized previously provided fingerprint.

17. The cessation system of claim 1, further comprising an ambient temperature sensor coupled to the hardware controller and an ambient pressure sensor coupled to the hardware controller, wherein the hardware controller is further configured to provide aerosolizer generation signals based at least in part on the signal from the ambient temperature sensor and the ambient pressure sensor.

18. The cessation system of claim 1, wherein the hardware controller provides aerosolizer control signals to control at least one of the first, second, and third aerosolizers to generate aerosol having a desired drop size based on the smoking cessation program information.

19. The cessation system of claim 1, wherein the hardware controller provides aerosolizer control signals to control the first, second, and third aerosolizers to generate desired aerosol mixture having a desired amount of a first substance, a second substance, and a third substance based on the smoking cessation program information.

20. The cessation system of claim 1, wherein the hardware controller is further configured to provide signals to the first, second, and third aerosolizer drivers to individually and dynamically control the first aerosolizer, the second aerosolizer, and the third aerosolizer, respectively, to produce the aerosol mixture having a concentration of a first substance, a concentration of a second substance, and a concentration of a third substance based on the smoking cessation program information.

21. The cessation system of claim 1, wherein the hardware controller is further configured to execute instructions to perform the smoking cessation program based on information determined from the flow sensor including puff duration, puff interval, puff volume, and/or puff profile.

* * * * *

UNITED STATES PATENT AND TRADEMARK OFFICE
CERTIFICATE OF CORRECTION

| | |
|---|---|
| PATENT NO. | : 12,114,695 B2 |
| APPLICATION NO. | : 17/650783 |
| DATED | : October 15, 2024 |
| INVENTOR(S) | : Robert Francis Jacobs, Jr. |

It is certified that error appears in the above-identified patent and that said Letters Patent is hereby corrected as shown below:

In the Specification

Column 19, Line 64, delete "drivers 110aic" and insert --drivers 110a-c--.

Column 22, Line 9, delete "<diameter≤10 m)." and insert --diameter≤10 μm).--.

Column 22, Line 11, delete "aerosolizers 161 161a-c." and insert --aerosolizers 161a-c.--.

Column 22, Line 56, delete "$FNR=1/(1+10^{-PH}/K_a)$" and insert --$FNR=1/(1+10^{-pH}/K_a)$--.

Column 23, Line 22, delete "FIG. 3A-3C." and insert --FIGS. 3A-3C.--.

In the Claims

Column 41, Line 37, delete "The smoking cessation program of claim 2" and insert --The cessation system of claim 2--.

Column 42, Line 25, delete "The smoking cessation system of claim 9" and insert --The cessation system of claim 9--.

Signed and Sealed this
Seventh Day of January, 2025

Derrick Brent
*Acting Director of the United States Patent and Trademark Office*